(12) United States Patent
Erdelmeir et al.

(10) Patent No.: US 7,381,416 B2
(45) Date of Patent: Jun. 3, 2008

(54) SELENOHYDROXY ACIDS AND THEIR DERIVATIVES, APPLICATIONS IN NUTRITION, COSMETICS AND PHARMACEUTICS

(75) Inventors: Irène Erdelmeir, Paris (FR);
Jean-Claude Michel, Colombes (FR);
Marc Moutet, Cachan (FR);
Jean-Claude Yadan, Montreuil Sous Bois (FR)

(73) Assignee: Tetrahedron SAS, Vincennes (FR)

( * ) Notice: Subject to any disclaimer, the term of this patent is extended or adjusted under 35 U.S.C. 154(b) by 9 days.

(21) Appl. No.: 11/187,617

(22) Filed: Jul. 22, 2005

(65) Prior Publication Data

US 2006/0105960 A1 May 18, 2006

(30) Foreign Application Priority Data

Jul. 23, 2004 (FR) .................................. 04 08181

(51) Int. Cl.
*A23L 1/30* (2006.01)
*A61K 31/095* (2006.01)
*C07F 11/00* (2006.01)

(52) U.S. Cl. .................. 424/401; 424/442; 426/648; 514/2; 514/8; 514/23; 514/120; 514/182; 514/546; 514/549; 514/557; 514/625; 514/706

(58) Field of Classification Search ............... None
See application file for complete search history.

(56) References Cited

U.S. PATENT DOCUMENTS

2004/0254239 A1* 12/2004 Abdel-Monem et al. ..... 514/494
2005/0163862 A1* 7/2005 Forceville et al. .......... 424/618

FOREIGN PATENT DOCUMENTS

| EP | 0804927 | 11/1997 |
|---|---|---|
| WO | WO 00/12101 | 3/2000 |
| WO | WO 00/067762 | 11/2000 |
| WO | WO 03/066071 | 8/2003 |

OTHER PUBLICATIONS

Gammelgaard et al. Combination of LC-ICP-MS . . . Talanta. May 1, 2003, vol. 59, Issue 6, pp. 1165-1171.*

International Search Report issued in International Application PCT/EP2005/008746 on Aug. 11, 2005 (5 pages).
May, S.W., "Selenium-based pharmacological agents: an update", Expert Opin. Investig. Drugs, vol. 11, No. 9, pp. 1261-1269 (2002).
Preliminary Search Report issued in FR 0408181 Mar. 3, 2005 (2 pages).

* cited by examiner

*Primary Examiner*—Jeffrey Edwin Russel
(74) *Attorney, Agent, or Firm*—Harness, Dickey & Pierce, P.L.C.

(57) ABSTRACT

The purpose of this invention is:
new selenohydroxy acid compounds and their derivatives;
their process for the preparation;
use of the new compounds as precursors of L(+)-selenomethionine and/or source of selenium in human or animal nutrition, in cosmetics and pharmaceutics;
and nutritional, cosmetic and pharmaceutical compositions containing them.

The new compounds that are the subject of this invention satisfy the general formula (I):

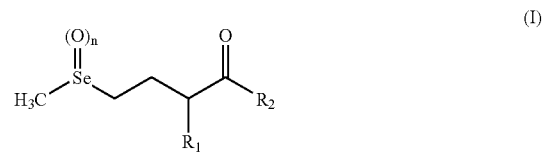

in which
n=0, 1 or 2,
$R_1$=OH, OCOR$_3$, OPO$_3$H$_2$, OPO(OR$_4$)(OR$_5$), or OR$_6$,
$R_2$=OH, R$_3$, or NHR$_7$,
$R_3$=particularly alkoxyl (C$_1$-C$_{26}$), ceramide 1, ceramide 2, ceramide 3, ceramide 4, ceramide 5, ceramide 6a and 6b, S-cysteinyl, or S-glutathionyl, carnitoyl, lipids, polyols,
OR$_4$=OR$_5$=particularly alkoxyl (C$_1$-C$_{26}$), ceramide 1, ceramide 2, ceramide 3, ceramide 4, ceramide 5, ceramide 6a and 6b, S-cysteinyl, or S-glutathionyl, carnitoyl, lipids, polyols,
OR$_6$=pyruvate, lactate, citrate, fumarate, maleate, myristate, palmitate, stearate, palmitoleate, oleate, linoleate, natural fatty acids, or 13-cis retinoate,
$R_7$=H, alkyl, natural amino acids, or natural amines.

32 Claims, 1 Drawing Sheet

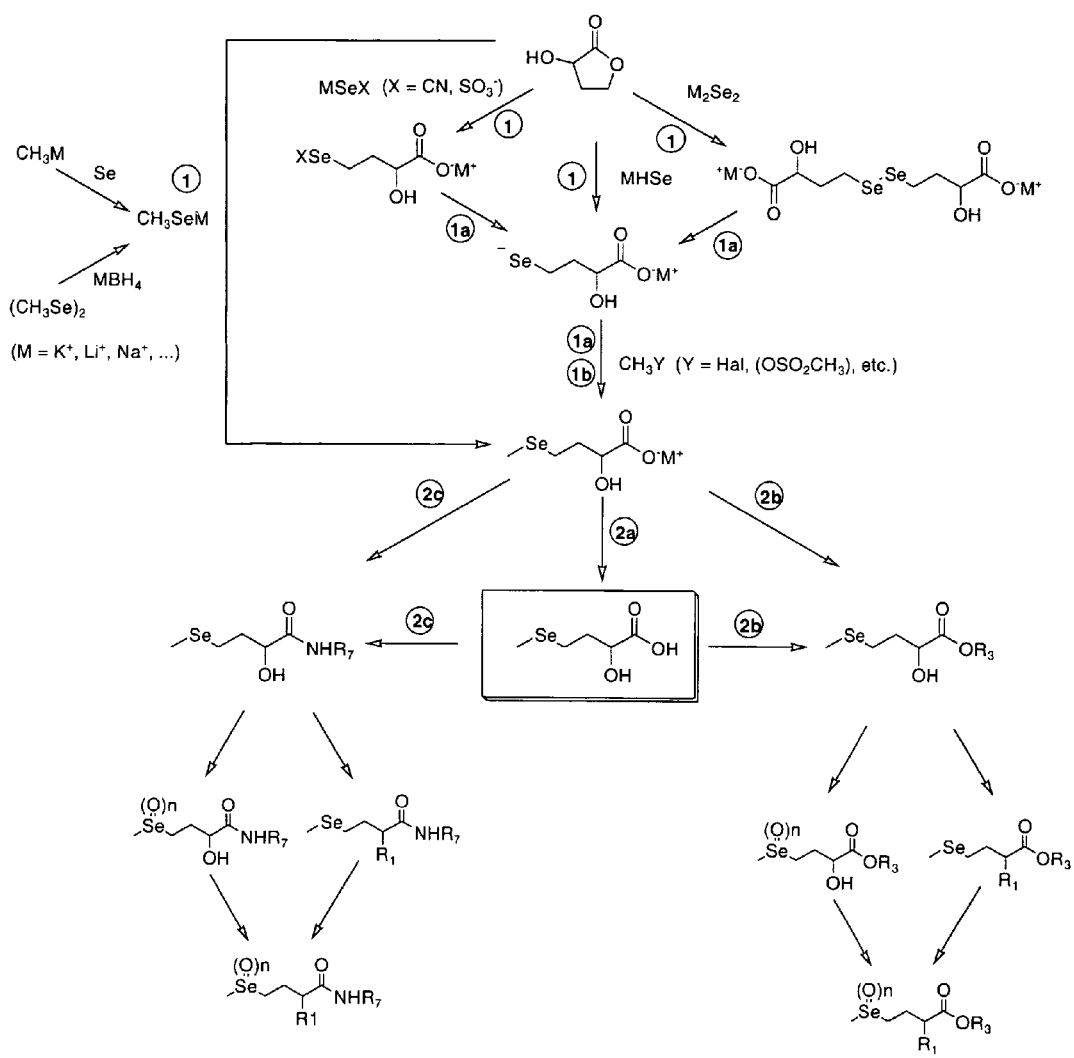

SELENOHYDROXY ACIDS AND THEIR DERIVATIVES, APPLICATIONS IN NUTRITION, COSMETICS AND PHARMACEUTICS

CROSS REFERENCE TO RELATED APPLICATIONS

The application claims priority to French Application No. 04 08 181, filed Jul. 23, 2004, which is incorporated by reference herein.

BACKGROUND OF THE INVENTION

The purpose of this invention is:

new selenohydroxy-acid compounds and their derivatives;

their process for the preparation;

their use as precursors of L(+)-selenomethionine and/or source of selenium in human or animal nutrition, in cosmetics and pharmaceutics;

and nutritional, cosmetic and pharmaceutical compositions containing them.

State of the Art

This invention relates to new selenohydroxy-acids (SHA) and their derivatives, their preparations and applications in nutrition, cosmetics and pharmaceutics. More particularly, this invention relates to the synthesis of 2-hydroxy-4-methylselenobutyric acid, its salts and esters and amides derived from 2-hydroxy-4-methylselenobutyric acid as selenomethionine precursors and particularly L(+)-selenomethionine precursors according to a biomimetic approach using enzymes with animal or human origin.

Selenium is a micro-nutrient essential particularly for Man and mammals (Wendel, A.; *Phosphorus, Sulfur Silicon Relat Elem.*; 1992; 67, 1-4, 405-415). It participates in the biosynthesis of selenoproteins such as Glutathion peroxydase, as well as Thioredoxine reductase and Selenoprotein, in the form of L(+)-selenocysteine or L(+)-selenomethionine (Muller, S. et al.; *Arch. Microbiol.*, 1997; 168; 421). According to FDA-RDAs 10th edition 1989 (*Selenium: its molecular biology and role in human health*; Hatfield, D. L. Eds; 2003; Kluwer Acad. Publishers; second edition; 299-31), Man's daily needs of selenium vary from 10-30 µg for a child to 40-70 µg for an adolescent-adult, these rates being higher particularly for women during pregnancy (65 µg/day) and during breast feeding (75 µg/day). The additional amount of L(+)-selenomethionine (2.7 µmoles of selenium equivalent) for breast feeding women significantly increases the concentration of selenium in their milk (McGuire, M. K. et al.; *Am. J. Clin. Nutr.*; 1993; 58; 5; 649).

Man is auxotrophic for L(+)-selenomethionine, which means that he is incapable of synthesising it. Therefore, the only way to obtain it is through food. Ideally, selenium should be absorbed in its natural form, in other words in organic form. Nevertheless, several forms of selenium may be used as a food complement; inorganic selenium for example such as sodium selenite; and organic selenium for example such as L(+)-selenomethionine. Knowing that more than 80% of total organic selenium in plants (particularly wheat, corn and soya) consists of L(+)-selenomethionine, this amino acid is the most appropriate and least toxic form of selenium, and is better than sodium selenite as an animal or human food complement (Schrauzer, G. N.; *J. Am. Coll. Nutrit.*; 2001; 20; 1; 1-4). L(+)-selenomethionine has better bio-availability and is much better tolerated than sodium selenite (Mony, M C et al.; *J. of Trace Elem. Exp. Med.*; 2000; 13; 367-380).

L(+)-selenomethionine has anti-oxidative properties due to the presence of selenium in its molecular structure (Tapiero H et al.; *Biomed. Pharmacother.*; 2003; 57; 3-4; 134-144). It has been shown that L(+)-selenomethionine very effectively traps peroxynitrite, an extremely toxic metabolite generated in all inflammatory situations and for which the deleterious action causes cell death (Assman, A. et al.; *Arch. Biochem. Biophys.*; 1998; 349; 201-203).

A selenium food complement proved to be very beneficial in many situations (nutritional deficiency, diseases, exposure to radiation, etc.). This is particularly true for children suffering from genetic diseases such as phenylcetonuria or hyperphenylalaninemia, since these children have low protein diets (Reilly, C. et al.; *Am. J. Clin. Nutr.*; 1990; 52; 150-165). Selenium in organic form such as L(+)-selenomethionine associated with vitamins has protective effects with regard to UV radiation in man (La Ruche et al.; *Photodermtol. Photoimmunol. Photomed.*; 1991; 8; 6; 232-235). L(+)-selenomethionine protects against the deleterious biological effects of high energy ionising radiation (Kennedy, A R et al.; *Free Rad. Biol. Med.*; 2004; 36; 2; 259-266).

Furthermore, several organoselenium derivatives have been effective in the prevention of some types of cancer in Man. In this context, it has been shown that L(+)-selenomethionine causes activation of a DNA repair system, mediated by the p53 tumour suppressor, thus reducing the accumulation of mutations in somatic cells (Seo, Y R et al.; *PNAS*; 2002, 89; 22;14548). It has been shown that a complement of up to 200 µg/Se/day of L(+)-selenomethionine in Man very significantly reduces the incidence of cancers such as cancer of the lungs, colorectal cancer and prostate cancer. Seven out of a total of eight clinical tests to evaluate the effect of selenium on the incidence of cancer gave positive results (Whanger, P D; *Br. J. Nutr.*; 2004; 91, 1, 11-28). This confirms the many studies carried out on animals.

Some rare selenohydroxy-acid derivatives have already been described as synthetic intermediates in the preparation of organic derivatives. These are essentially arylselenohydroxy-acid derivatives. For example, this is the case for the methyl ester of 2-hydroxy-4-phenylselenobutyric acid (J.-G. Boiteau, *Organic Letters*, 2001, 3 (17), 1737-2740). Furthermore, a selenoxide of 2-hydroxy-4-methylselenobutyric acid has been suggested as an intermediate of oxydative degradation of L(+)-selenomethionine (Gammelgaard, B. et al.; *Talenta*; 2003; 59; 1165-1171).

Surprisingly, 2-hydroxy-4-methylselenobutyric acid itself, its salts and its ester and amide derivatives, are not known. Unlike arylselenohydroxy acid derivatives, these latter compounds may represent potential precursors of selenomethionine. After an enzymatic or chemical transformation, 2-hydroxy-4-methylselenobutyric acid, its salts and its ester and amide derivatives, after eventual hydrolysis, can lead to selenomethionine according to the following transformation

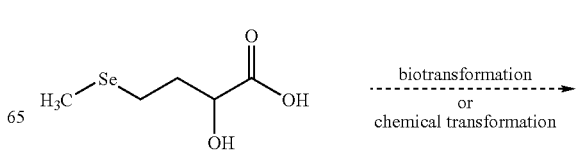

-continued

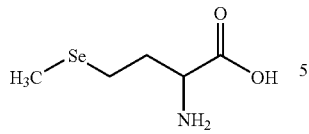

Furthermore, 2-hydroxy-4-methylsulfobutyric acid is known as a methionine precursor for food (WO 9636598; 21 Nov. 1996).

One of the purposes of this invention is to create new compounds containing selenium that, after being administered to man or to animal, may be precursors of selenomethionine, and therefore sources of selenium for the organism. Compounds according to the invention can penetrate inside tissues or cells to be biotransformed into selenomethionine or derivatives so that selenium can be incorporated into proteins of the organism.

These purposes are achieved through this invention that is based on the design of new selenohydroxy-acid derivatives and their esters and amides, which are biotransformed by enzymes present in animal or human cells to generate selenomethionine. This has been exemplified by the Applicant.

DRAWINGS

The drawings described herein are for illustration purposes only and are not intended to limit the scope of the present disclosure in any way.

FIG. 1 represents a process for the preparation of new selenohydroxy-acids, their esters and amide derivatives, according to certain aspects of the present disclosure.

DESCRIPTION OF THE INVENTION

Therefore, the purpose of this invention is to:
1) solve the new technical problem that consists of supplying new selenohydroxy-acids, ester and amide derivatives, as selenomethionine precursors, thus forming the active constituents of nutritional, cosmetic and pharmaceutical compositions;
2) solve this new technical problem using a solution that includes a method for preparation of these new derivatives.

The technical problems mentioned above are solved simultaneously by this invention for the first time, in a very easy and economic manner, the method for preparation of the said new derivatives being high-yielding and very simple to implement.

According to the first aspect of this invention, the purpose is new selenohydroxy-acids of general formula (I):

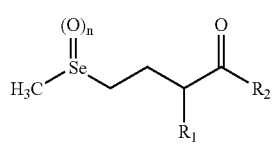

(I)

in which
n=0, 1 or 2
$R_1$=OH, $OCOR_3$, $OPO_3H_2$, $OPO(OR_4)(OR_5)$, or $OR_6$,
$R_2$=OH, $R_3$, or $NHR_7$,
$R_3$=alkoxyl ($C_1$-$C_{26}$), ceramide 1, ceramide 2, ceramide 3, ceramide 4, ceramide 5, ceramide 6a and 6b, S-cysteinyl, or S-glutathionyl, or

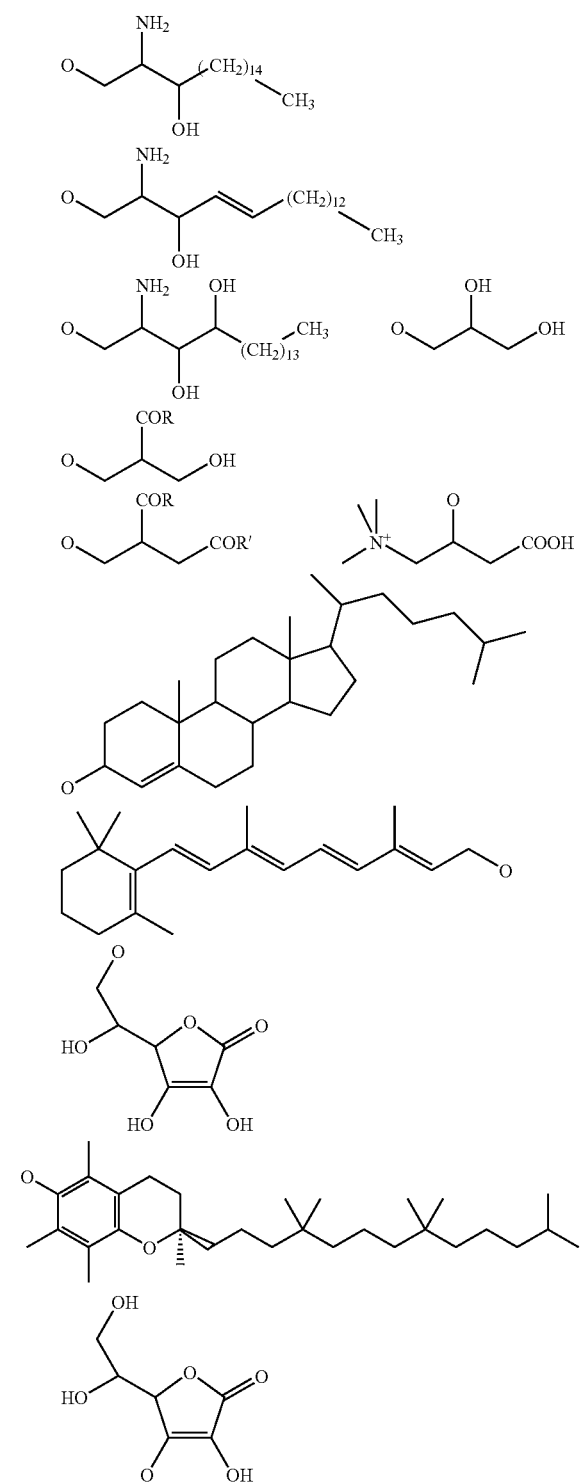

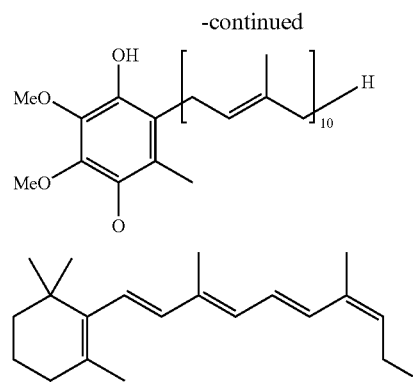
OR$_4$=alkoxyl (C$_1$-C$_{26}$), ceramide 1, ceramide 2, ceramide 3, ceramide 4, ceramide 5, ceramide 6a or 6b,
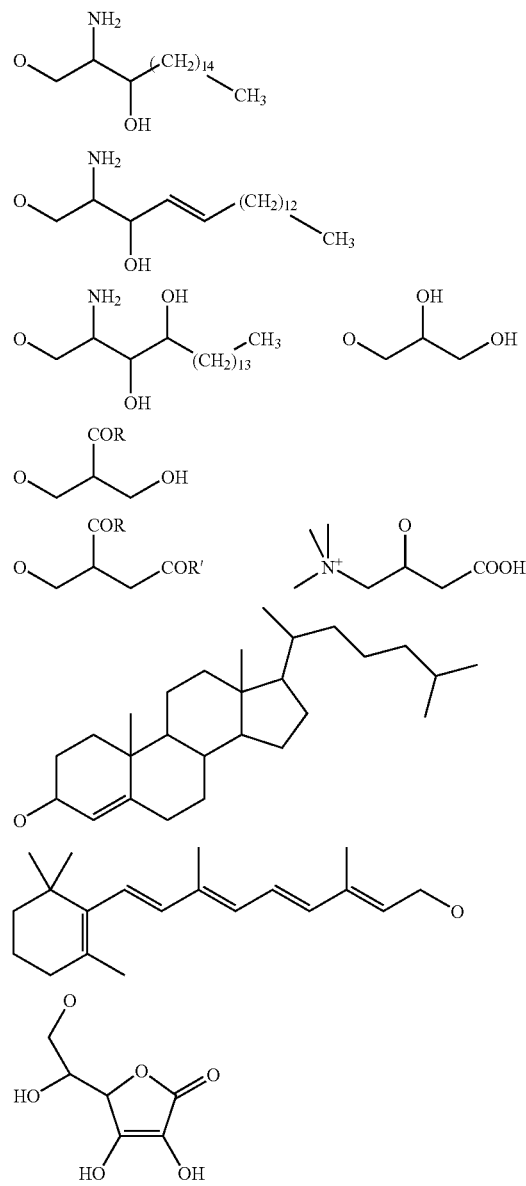
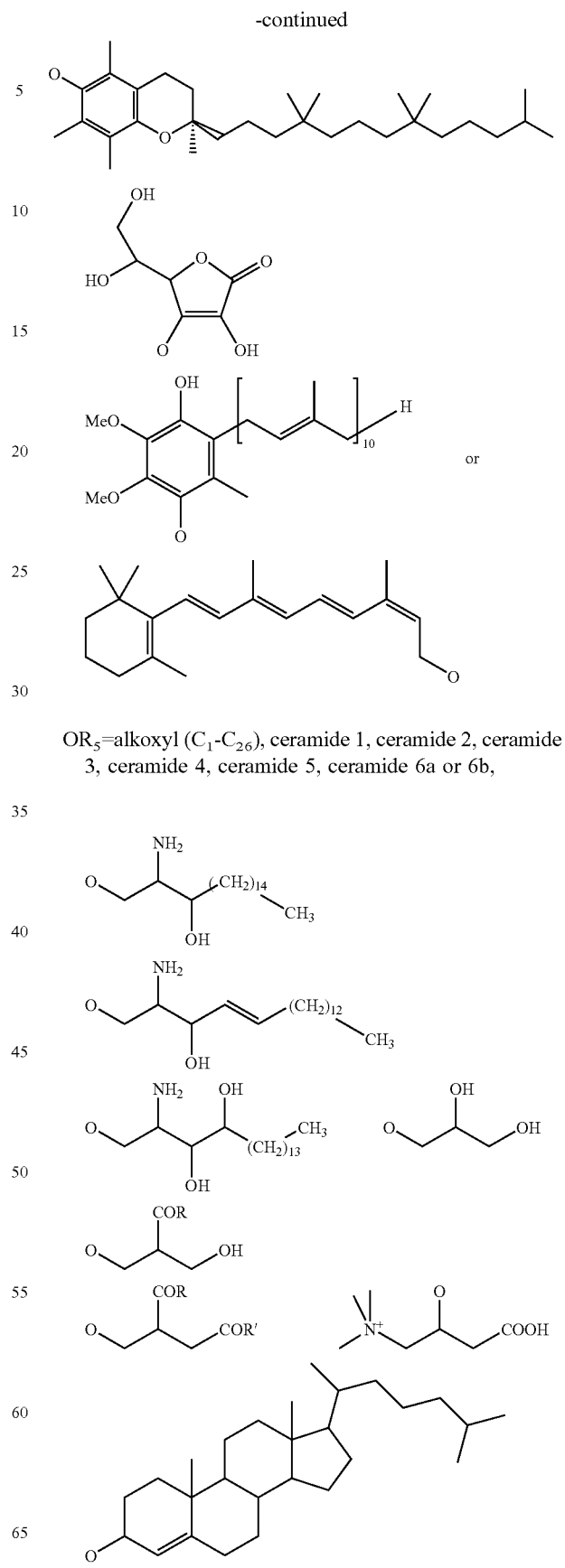
OR$_5$=alkoxyl (C$_1$-C$_{26}$), ceramide 1, ceramide 2, ceramide 3, ceramide 4, ceramide 5, ceramide 6a or 6b,

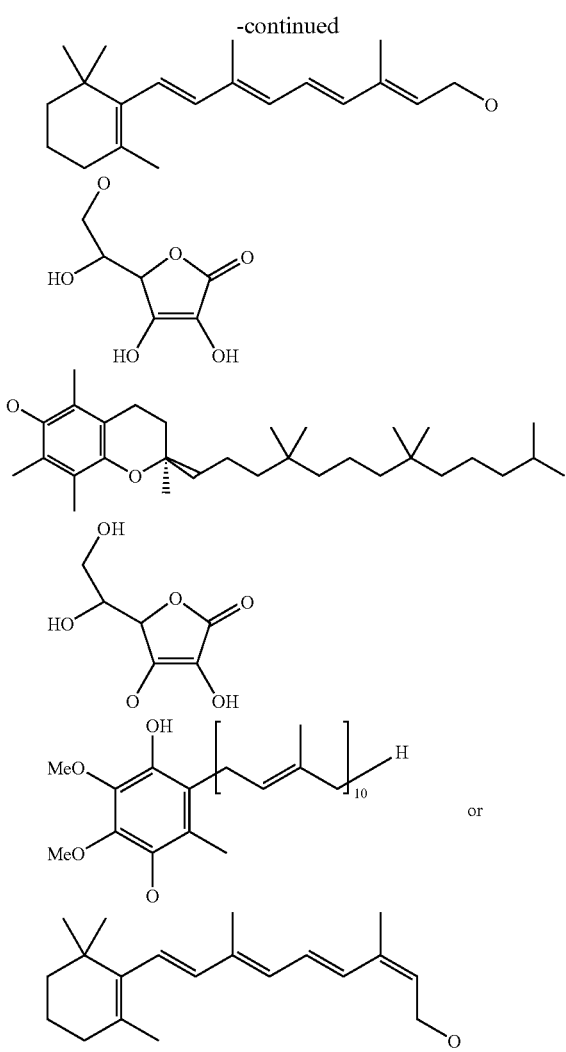

$OR_6$=pyruvate, lactate, citrate, fumarate, maleate, myristate, palmitate, stearate, palmitoleate, oleate, linoleate, natural fatty acids, or 13-cis retinoate, $R_7$=H, alkyl, natural amino acids, or natural amines, it being understood that when n=1 and $R_2$=OH, $R_1$ cannot be OH.

The invention encompasses all position isomers, geometric isomers, stereo-isomers, diastereoisomers and enantiomers, particularly for the selenium and carbon atom carrying the $R_1$, group and for radicals $R_1$ to $R_7$, and all oligomers (dimers, trimers, etc.) and linear or ramified, acyclic or cyclic polymers, obtained between two or several molecules of selenohydroxy-acid derivatives described according to the invention by an esterification reaction between alcohol and carboxylic acid functions that may be present, taken separately or mixed. It also encompasses all pharmaceutically acceptable acid and base addition salts of the said compounds of general formula (I), particularly sodium and calcium and magnesium salts.

Among the compounds of general formula (I), the invention has especially as object the following compounds of general formula (I):

compounds characterized in that n is 0;
compounds characterized in that $R_1$ represents OH, $OCOR_3$, $OR_6$;
compounds characterized in that $R_2$ is chosen from the group composed of OH, $NHR_7$, glyceroyl, monoacylglyceroyl, diacylglyceroyl, coenzyme Q, retinoyl, cholesteroyl, alpha-tocopheroyl, carnitinoyl, sphinganine, sphingosine, phytosphingosine, ceramide 1, ceramide 2, ceramide 3, ceramide 4, ceramide 5, ceramide 6a and 6b, ascorbate, S-cysteinyl, S-glutathionyl, $R_7$ being as defined above;
compounds prepared in the experimental part, particularly (D,L)-, L- and D-2-hydroxy-4-methylselenobutyric acid.

Pharmaceutically acceptable acids non-limitatively include mineral acids such as hydrochloric, hydrobromic, hydriodic, sulfuric, tartric, phosphoric or organic acids such as formic acid, acetic acid, trifluoro-acetic acid, propionic acid, benzoic acid, maleic acid, fumaric acid, succinic acid, citric acid, oxalic acid, glyoxylic acid, aspartic acid, alcanesulfonic acids such as methane-sulfonic acid, trifluoromethane-sulfonic acid, ethane-sulfonic acid, aryl-sulfonic acids such as benzene and paratoluene-sulfonic acids. Pharmaceutically acceptable bases non-limitatively include mineral bases such as sodium, lithium, calcium, potassium, magnesium, ammonium or zinc hydroxides, carbonates of alkaline metals or alkaline earths such as carbonates and bicarbonates of sodium, lithium, calcium, potassium, magnesium, ammonium or zinc and organic bases such as methylamine, propylamine, trimethylamine, diethylamine, triethylamine, N,N-dimethylethanolamine, tris(hydroxymethyl)aminomethane, ethanolamine, pyridine, picoline, dicyclohexyl-amine, morpholine, procene, lysine, arginine, histidine, N-methylglucamine or phosphonium salts such as alkyl-phosphonium salts, aryl-phosphonium salts, alkyl-aryl-phosphonium salts, alkenyl-aryl-phosphonium salts or quaternary ammonium salts such as tetra-n-butyl-ammonium salts.

In formula (I) above:
alkyl refers to a group comprising 1 to 26 linear or cyclic, possibly ramified and possibly fluorinated or polyfluorinated carbon atoms, possibly comprising one or several double carbon-carbon bonds, for example such as methyl, ethyl, isopropyl, trifluoromethyl, linoleyl, linolenyl, palmitoyl.
alkoxyl refers to a group derived from a primary, secondary or tertiary alcohol comprising 1 to 26 linear or cyclic, possibly ramified and possibly fluorinated or polyfluorinated carbon atoms, possibly comprising one or several double carbon-carbon bonds, for example such as methoxyl, ethoxyl, isopropoxyl, trifluoromethoxyl, linoleoxyl, linolenoxyl, palmitoxyl.
ceramide type radical structures are described particularly in <<Cosmetic Lipids and the Skin Barrier>>, Thomas Förster Ed. 2002, Marcel Dekker, Inc., p 2, FIG. 2.
natural refers to any corresponding compound existing in the metabolism of organisms from the vegetable and animal world and in man (Steglich W., *Römpp Encyclopedia Natural Products*, G. Thieme ed.)
oligomer refers to any compound composed of a sequence of 2 to 15 monomers connected to each other through an ester type bond.
polymer refers to any compound consisting of a sequence of more than 15 monomers connected together through an ester type bond.

Another purpose of the invention is a process for the preparation of new selenohydroxy-acids and their ester and amide derivatives of general formula (I), described in attached FIG. 1, characterized in that it comprises at least one of the following steps:

1) the reaction of (D,L)-2-$R_1$-butyrolactone or one of its enantiomers (D or L), where $R_1$ is as defined above, either with an alkaline methylselenolate salt of formula (IIa)

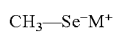 (IIa)

in which M represents an atom of an alkaline metal, to obtain a compound of formula (Ia) in the form of an alkaline salt:

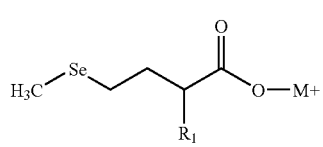 (Ia)

in which M and $R_1$ are as defined above;
or with an alkaline selenium reagent of formula (IIb)

 (IIb)

in which M represents an atom of an alkaline metal, to obtain a compound of formula (III) in the form of an alkaline salt:

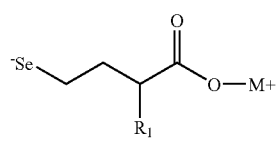 (III)

in which M and $R_1$ are as defined above;
or with an alkaline selenium reagent of formula (IIc)

MSeX (IIc)

in which M is as defined above and X represents a CN radical, or $SO_3M$, or aryl-$SO_2M$, to obtain a compound of formula (IIIa) in the form of an alkaline salt:

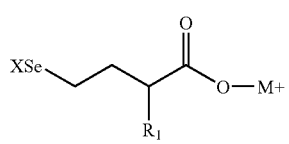 (IIIa)

in which M, $R_1$ and X are as defined above;
or with an alkaline selenium reagent of formula (IId)

MSeSeM (IId)

in which M is as defined above, to obtain a compound of formula (IIIb) in the form of an alkaline salt:

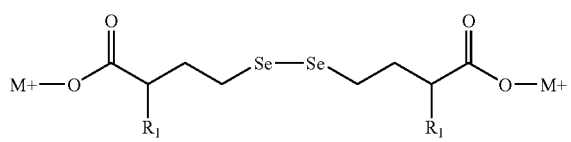 (IIIb)

makes the intermediate compound of formula (IIIa) or (IIIb) react with a reducing agent, to obtain a compound of formula (III)

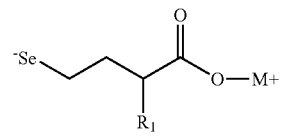 (III)

and then treats the compound of formula (III) with a methylation agent of formula (IV):

$CH_3$—Y (IV)

in which Y represents a halogen atom, or an $OSO_2CH_3$, $OSO_2$-p-tolyl, or $OCO_2CH_3$ group to obtain the compound of formula (Ia) mentioned above,

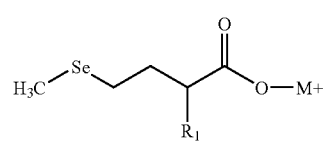 (Ia)

2) if desired one or even several reactions or series of reactions described below:
acidification of the reaction medium to obtain the acid corresponding to formula (I);
esterification of the acid of formula (I) or its alkaline salt of formula (Ia) with an alcohol or an alkyl halide to obtain the compound of general formula (I) in which $R_2$=$R_3$ is as defined above;
amidification of the acid of formula (I) or its alkaline salt of formula (Ia) with an appropriate amine of formula $R_7NH_2$, in which $R_7$ is as defined above, to obtain the compound of general formula (I) in which $R_2$=$NHR_7$ is as defined above;
esterification, when $R_1$=OH, of the hydroxyl function by an appropriate acid to obtain the compound of general formula (I) in which $R_1$ is different from the OH group;
oxidation leading to the selenoxide or selenone derivative to obtain the compound of general formula (I) in which n is equal to 1 or 2;
salification by an acid or a base.

According to one advantageous embodiment of the process according to the invention:
the nucleophile selenium reagent is:
either a methyl selenolate salt which is possibly generated in situ:
or produced from selenium metal Se(0) and an alkyl salt in an aprotic solvent, for example such as tetrahydrofurane (THF);
or from a dimethyl diselenide $(CH_3Se)_2$ in the presence of a reducing agent, for example such as sodium borohydride in an aprotic solvent for example such as THF;
or a selenocyanate salt such as potassium selenocyanate which may be generated in situ:
or from selenium metal Se(0) and an a cyanide salt for example such as potassium cyanide,
or added to the medium as such,
or a selenide or diselenide salt for example such as sodium or lithium selenide or diselenide, or a selenosulfate salt for example such as sodium selenosulfate.

An aprotic polar solvent is used, for example such as THF. The reducing agent that is made to react with the compound of formula (IIIa) or (IIIb) is preferably an alkaline borohydride. The subsequent reactions leading to different compounds of formula (I), either acidification, esterification, amidification, oxidation, salification, are done under conditions known to those skilled in the art. In particular, the purpose of the invention is a method as defined above, characterized in that the starting point is 2-hydroxybutyrolactone. 2-$R_1$-butyrolactone is obtained by esterification of 2-hydroxybutyrolactone under conditions known to those skilled in the art. Intermediate compounds of formulae (III), (IIa) and (IIIb) as defined above are new and consequently are included in the invention.

Another purpose of the invention is a process for the preparation of L-(+)-selenomethionine starting from 2-hydroxy-4-methylseleno-butyric acid of formula (I) or one of its alkaline salts of formula (Ia) described in the above method. Through this aspect, the Applicant shows the capacity of compounds of general formula (I) to act as precursors of L-(+)-selenomethionine, either directly or after enzymatic or non-enzymatic hydrolysis. The innovative nature of this new process consists in a combination of a synthetic chemical approach in the first part of the method with a biomimetic approach that uses enzymes when applicable, particularly mammal enzymes in the second part of this method.

The method includes the following essential steps:

1) oxidation of 2-hydroxy-4-methylseleno-butyric acid of formula (I) or one of its alkaline salts of formula (Ia) described in the above method, either by an oxydo-reductase type enzyme, for example such as an alcohol dehydrogenase, or by a chemical method based on action by an appropriate oxidation reagent to obtain the corresponding cetoacid of formula (V);

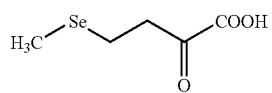
(V)

2) transamination of the compound of formula (V) either by an enzymatic method using a transaminase such as an amino-acid transaminase, or chemically under reducing amination conditions to obtain L-(+)-selenomethionine.

These two enzymatic reactions may be performed either separately with the possibility of isolating the intermediate compound of formula (V), or <<one-pot>> to obtain L-(+)-selenomethionine directly. The oxydo-reductase type enzyme may particularly be an alcohol dehydrogenase. In particular, the transaminase is an amino-acid transaminase. Particularly interesting for this purpose, transamination of 2-ceto-4-methylselenobutyric acid obtained by degradation of L(+)-selenomethionine, was described by C. Blarzino et al. using a purified glutamine transaminase starting from beef liver (*Biochem. Mol. Biol. Int.*; 1994; 32, 1, 79-86).

Chemical oxidation of 2-hydroxy-4-methylselenobutyric acid is done particularly using a sulfonium dimethyl chloride type reagent [$(Me)_2ClS^+$, $Cl^-$] and transamination of the compound of formula (V) is done chemically under reducing amination conditions well known to those skilled in the art. Another purpose of the invention is the use of compounds of general formula I and their salts as a source of selenomethionine, particularly L(+) selenomethionine, and/or selenium in man or animal.

In particular, this means use of the said compounds of general formula (I) as:

L-(+)-selenomethionine precursors either directly or after in vivo enzymatic hydrolysis;

selenium sources, in order to compensate for partial or total lack of selenium;

food complements or additives for making nutritional compositions for human or animal food (more particularly cattle, sheep, pigs, horses, dogs and cats and poultry);

components for making cosmetic compositions;

active constituents for making pharmaceutical compositions adapted particularly to the prevention and treatment of all physiopathological conditions, in which a complement of L-(+)-selenomethionine, either alone or in co-administration with an anticancer agent, has been shown to be beneficial, and including particularly:

prevention and treatment of cancers such as prostate, lungs, colon and skin cancers;

prevention and treatment of either UV or ionising radiation effects;

prevention and treatment of pathologies related to the overproduction of peroxynitrite, a very toxic metabolite of nitric oxide NO, as is the case particularly in inflammatory pathologies;

and also as:

additives to a pharmaceutical active constituent to modulate its toxicity and/or its therapeutic efficiency, for example in the use of particularly toxic anti-tumour agents.

A particular purpose of the invention is the use as described above, characterized in that the compounds of general formula (I) or their salts are presented in the form of foods complements or additives for human or animal food. Another purpose of the invention is the use of compounds of general formula (I) and their pharmaceutically acceptable salts as active constituents for manufacturing pharmaceutical compositions, or the use of compounds of general formula (I) and their salts as components for the manufacture of cosmetics compositions, characterized in that the compounds used belong to the general formula (I') corresponding to the general formula (I)

in which n=0, 1 or 2, $R_1$=$OCOR_3$, $OPO_3H_2$, $OPO(OR_4)(OR_5)$, or $OR_6$, $R_2$=$R_3$, or $NHR_7$, $R_3$=ceramide 1, ceramide 2, ceramide 3, ceramide 4, ceramide 5, ceramide 6a and 6b, S-cysteinyl, or S-glutathionyl, or

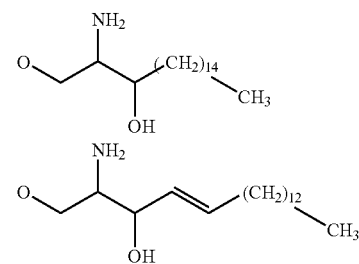

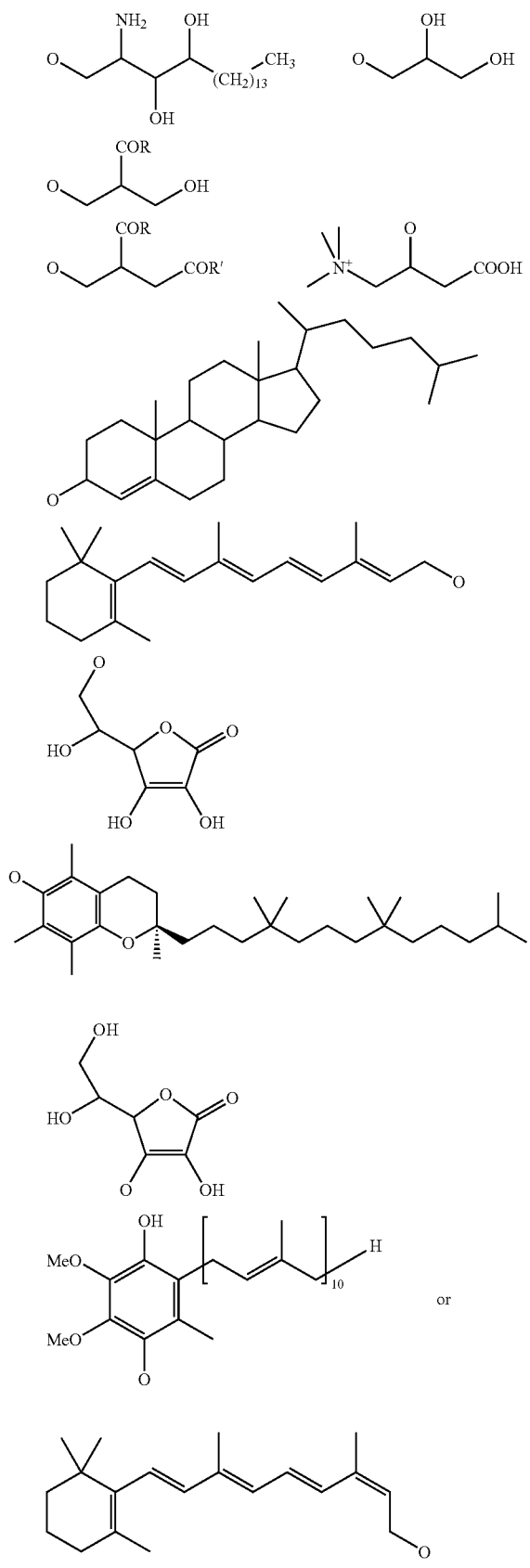
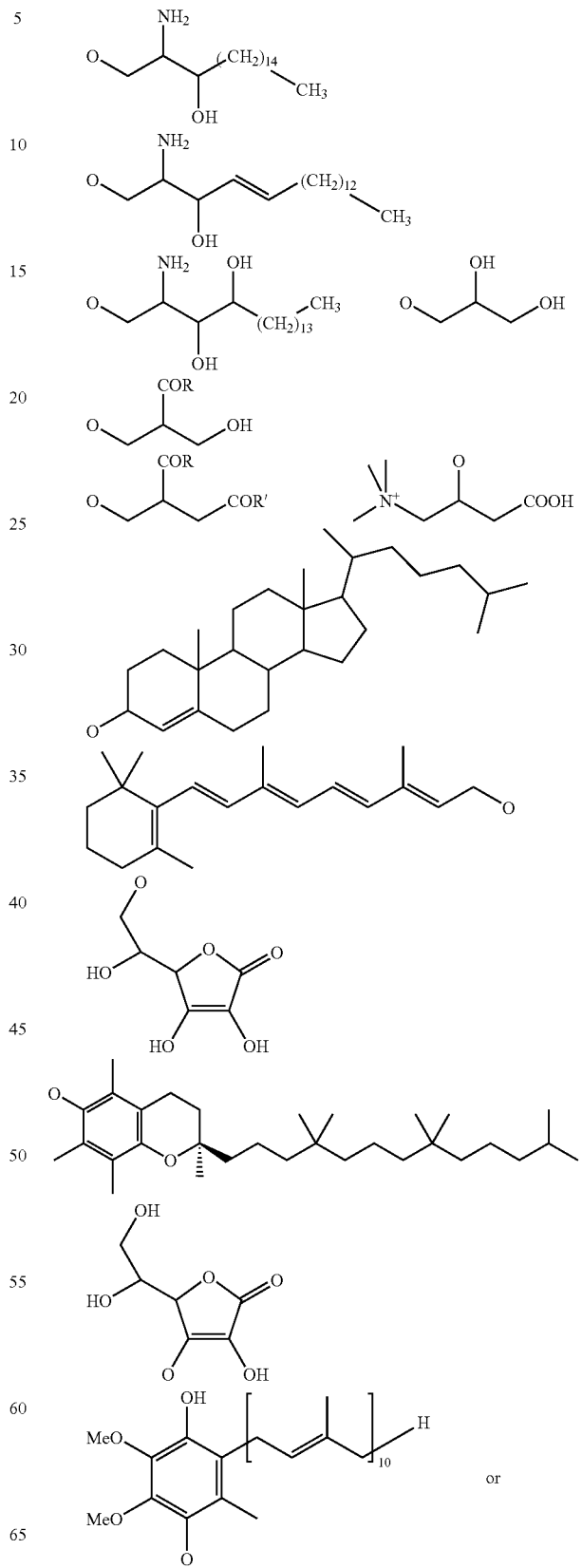
$OR_4$=alkoxyl ($C_1$-$C_{26}$), ceramide 1, ceramide 2, ceramide 3, ceramide 4, ceramide 5, ceramide 6a or 6b,

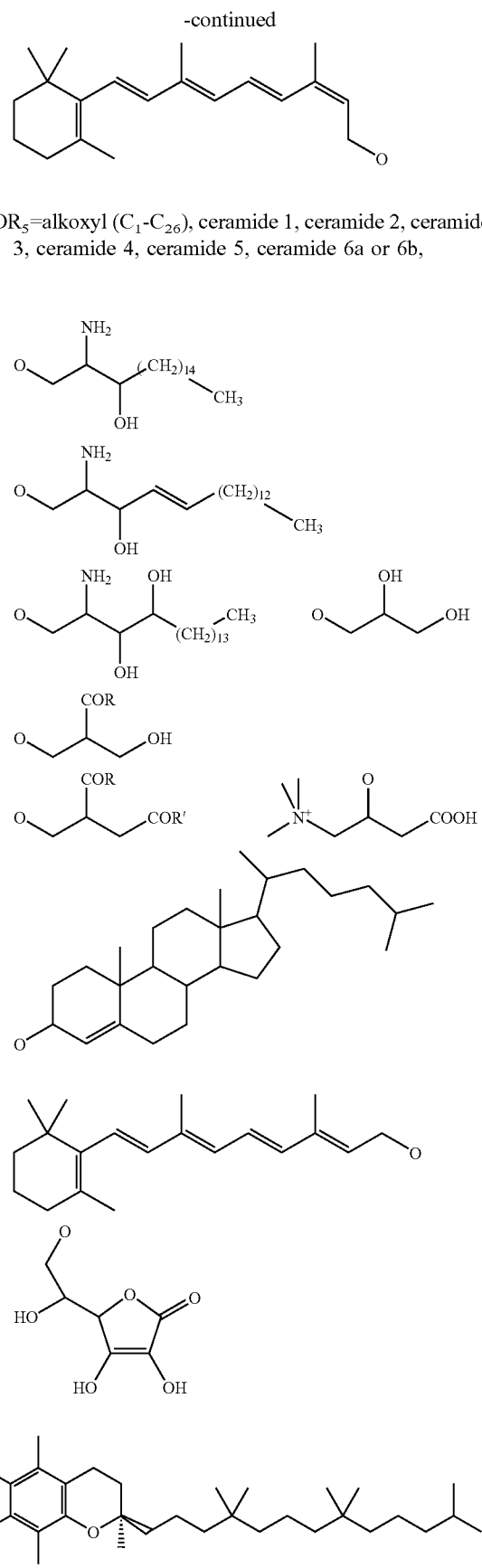

OR$_5$=alkoxyl (C$_1$-C$_{26}$), ceramide 1, ceramide 2, ceramide 3, ceramide 4, ceramide 5, ceramide 6a or 6b,

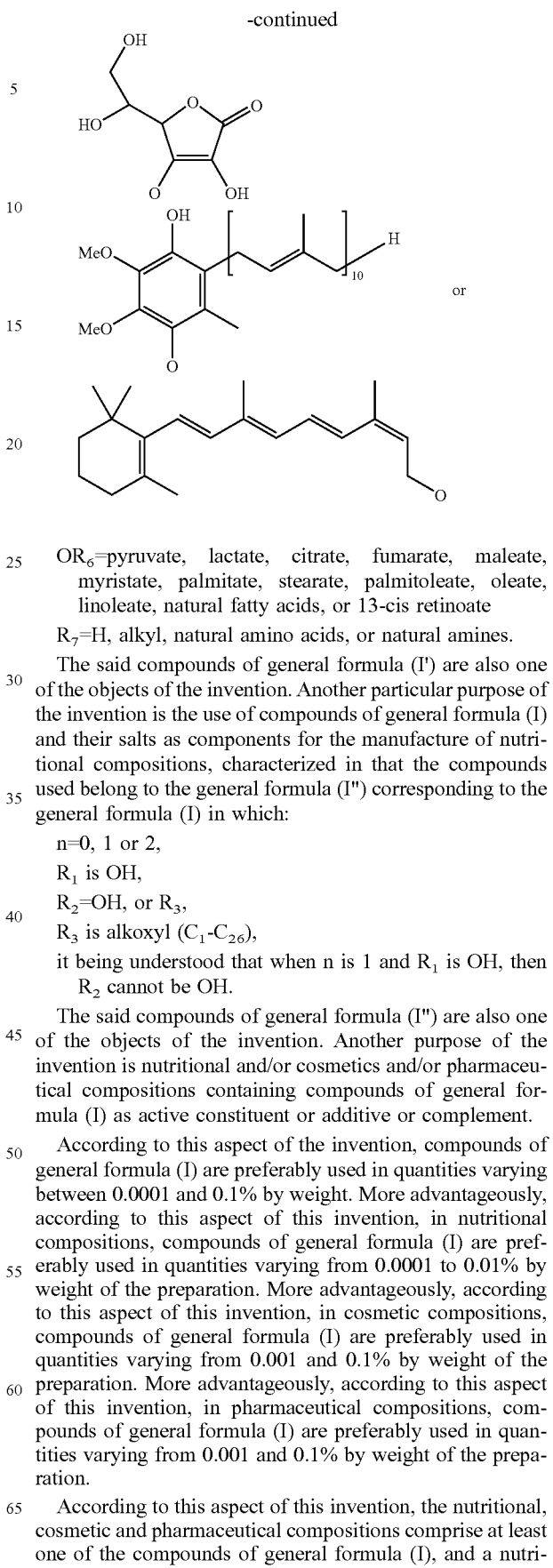

OR$_6$=pyruvate, lactate, citrate, fumarate, maleate, myristate, palmitate, stearate, palmitoleate, oleate, linoleate, natural fatty acids, or 13-cis retinoate R$_7$=H, alkyl, natural amino acids, or natural amines.

The said compounds of general formula (I') are also one of the objects of the invention. Another particular purpose of the invention is the use of compounds of general formula (I) and their salts as components for the manufacture of nutritional compositions, characterized in that the compounds used belong to the general formula (I") corresponding to the general formula (I) in which:

n=0, 1 or 2,

R$_1$ is OH,

R$_2$=OH, or R$_3$,

R$_3$ is alkoxyl (C$_1$-C$_{26}$), it being understood that when n is 1 and R$_1$ is OH, then R$_2$ cannot be OH.

The said compounds of general formula (I") are also one of the objects of the invention. Another purpose of the invention is nutritional and/or cosmetics and/or pharmaceutical compositions containing compounds of general formula (I) as active constituent or additive or complement.

According to this aspect of the invention, compounds of general formula (I) are preferably used in quantities varying between 0.0001 and 0.1% by weight. More advantageously, according to this aspect of this invention, in nutritional compositions, compounds of general formula (I) are preferably used in quantities varying from 0.0001 to 0.01% by weight of the preparation. More advantageously, according to this aspect of this invention, in cosmetic compositions, compounds of general formula (I) are preferably used in quantities varying from 0.001 and 0.1% by weight of the preparation. More advantageously, according to this aspect of this invention, in pharmaceutical compositions, compounds of general formula (I) are preferably used in quantities varying from 0.001 and 0.1% by weight of the preparation.

According to this aspect of this invention, the nutritional, cosmetic and pharmaceutical compositions comprise at least one of the compounds of general formula (I), and a nutritionally, cosmetically and pharmaceutically acceptable medium respectively. In particular these media may consist of:
- an aqueous or alcohol solution or an oil,
- a water/oil or oil/water emulsion, a microemulsion,
- an aqueous gel,
- a dispersion of vesicles, microcapsules, micro- or nanoparticles,
- a solid medium composed of one or several excipients that may be selected from among vitamins, natural anti-oxidants, mineral salts, mono-, di- or polysaccharides and particularly folic acid, vitamins $B_6$, E or C, lactose, starch. This solid medium composed of one or several excipients as defined above and comprising at least one of the compounds of general formula (I), may be formulated in the form of a capsule, a tablet or a powder.

These media are given as non-limitative examples simply for illustration purposes and therefore in no way limit the scope of the invention, and may be nutritional liquids for example such as food milk, fruit juice, syrups and also baby milk, or a parenteral solution, table salt or in general any food with a controlled complement of selenium.

According to this aspect of this invention, the nutritional, cosmetic and pharmaceutical compositions containing at least one of the compounds of general formula (I) as the active constituent, complement or additive may be administered orally, parenterally, topically (including transdermally, nasally, ocularly), or by inhalation, depending on the case. Quantities of the different constituents of these compositions apart from compounds of general formula (I), are those usually used for the applications mentioned.

In particular, one purpose of the invention is cosmetic and pharmaceutical compositions containing at least one of the compounds of general formula (I') as defined above as an active constituent or an additive or complement. Finally, another purpose of the invention is nutritional compositions containing at least one of the compounds of general formula (I") as defined above as the active constituent.

The examples mentioned below and the attached scheme for the method according to the invention are supplied simply for illustration purposes and in no way limit the scope of the invention. All reactions take place under an inert argon atmosphere except when mentioned otherwise.

EXAMPLE 1

Preparation of L-2-hydroxy-4-methylselenobutyric acid 5.6 mL (9 mmol) of a solution of methyllithium in ether (1.6 M) is added dropwise to a suspension of 645 mg (8.2 mmol) of selenium in 30 mL of anhydrous THF, at 0° C. The suspension firstly becomes dark brown then reddish and at the end of the addition a clear, homogenous and colourless solution is obtained. After stirring for 15 min. at 0° C., 0.77 mL (1.0 g, 9.8 mmol) of S-(−)-alpha-hydroxybutyrolactone is added. A white precipitate is quickly formed. Stirring is continued at 0° C. for 15 minutes, and the reaction mix is then allowed to warm up to ambient temperature. After 24 h at ambient temperature and 24 h at 40° C., the heterogeneous mix is cooled to 5° C. The precipitate is filtered and then washed with 4×25 mL of diethylic ether. 1.05 g of a white powder is obtained. This compound is dissolved in 20 mL of NaOH, and the solution obtained is washed with 4×25 mL of diethylic ether. The aqueous phase is then acidified with concentrated HCl to a pH=1, and is then extracted with 10×25 mL of dichloromethane. After drying ($Na_2SO_4$), filtration and evaporation, the result is 890 mg (55%) of the required compound with a purity of about 90-95% ($^1$H-RMN, $CDCl_3$) in the form of a colourless oil that crystallises when cold. The raw product is recrystallised in 5 mL of toluene to obtain 636 mg (40%) of L-2-hydroxy-4-methylselenobutyric acid with a purity of about 93-95% ($^1$H-RMN, $CDCl_3$) in the form of a colourless powder.

$^1$H-RMN ($CDCl_3$, 300 MHz): δ (ppm)=2.02 (s, 3H); 2.08 (m, 1H); 2.22 (m, 1H); 2.70 (m (sym.), 2H); 4.41 (dd, J=8 Hz, J=4 Hz, 1H, α-H).

Low intensity signals are detected at δ (ppm)=2.60 (m); 4.25 (m); 4.50 (m).

$R_f$ ($SiO_2$, cyclohexane/ethyl acetate, 50/50+1% $CF_3COOH$): 0.26.

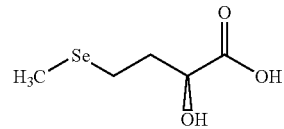

EXAMPLE 2

Preparation of dicyclohexylammonium L-2-hydroxy-4-methylseleno-butyrate 600 mg (3 mmol) of the previous compound described in example 1, is dissolved in 4 mL of diethylic ether, and 1.2 mL (6 mmol) of dicyclohexylamine is added dropwise. A colourless precipitate is formed immediately that is filtered and washed with 2×20 mL of diethylic ether. After recrystallisation in 5 mL of an ethyl acetate/cyclohexane mix (50/50), 750 mg (66%) of the required compound is obtained with purity >98% ($^1$H-RMN, $CDCl_3$) in the form of colourless crystals.

$^1$H-RMN ($CDCl_3$, 300 MHz): δ (ppm)=1.18-2.20 (m, 22H); 2.00 (s, 3H, $SeCH_3$); 2.38 (m, 2H); 2.97 (m, 2H); 3.94 (dd, J=8 Hz, J=4 Hz, 1H, α-H).

$^{13}$C-RMN ($CDCl_3$, 75.5 MHz): δ (ppm)=3.9; 21.5; 24.7; 25.1; 29.2; 30.9; 36.2; 52.7; 71.6; 178.6.

MS (electrospray): m/z (%)=182 ($NH_2(cyclo-hexyl)_2^+$). m/z (%)=197 ($CH_3SeCH_2CH_2CHOHCO_2^-$).

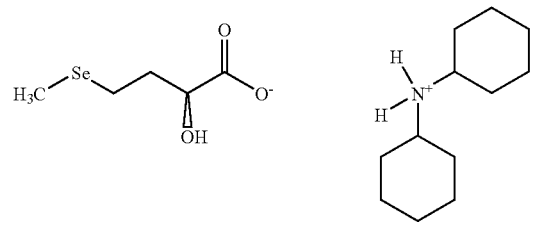

EXAMPLE 3

Preparation of L-2-hydroxy-4-methylselenobutyric acid

L-2-hydroxy-4-methylselenobutyric acid is obtained in the form of colourless crystals by solubilisation of 750 mg (2 mmol) of the previous compound described in example 2, in 10 mL of water, acidification with concentrated HCl until pH=1 and extraction with 8×20 mL of diethylic ether. After drying (Na$_2$SO$_4$), filtration and evaporation, the result is 365 mg of the required compound in the form of colourless crystals with purity >98% ($^1$H-RMN, CDCl$_3$).

pF (° C.): 47.4-48.0.

$^1$H-RMN (CDCl$_3$, 300 MHz): δ (ppm)=2.02 (s, 3H, SeCH$_3$); 2.08 (m, 1H); 2.22 (m, 1H); 2.70 (m sym.), 2H); 4.43 (dd, J=8 Hz, J=4 Hz, 1H, α-H).

$^{13}$C-RMN (CDCl$_3$, 75.5 MHz): δ (ppm)=4.1; 20.3; 33.9; 69.9; 177.3.

MS (electrospray): m/z (%)=197 (CH$_3$SeCH$_2$CH$_2$CHOHCO$_2$$^-$).

R$_f$ (SiO$_2$, cyclohexane/ethyl acetate, 50/50+1% CF$_3$COOH): 0.26.

[α]$_D$=−20.5±1 (c=1, EtOH).

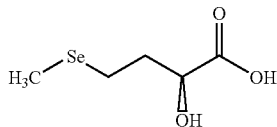

EXAMPLE 4

Preparation of D-2-hydroxy-4-methylselenobutyric acid

D-2-hydroxy-4-methylselenobutyric acid is obtained using the method described in Example 1 for the <<L>> enantiomer with a yield of 57% in the form of colourless crystals, but by adding 0.76 mL (1.0 g, 9.8 mmol) of R-(+)-alpha-hydroxybutyrolactone to the solution of lithiomethylselenolate.

pF (° C.): 46.0-47.0° C.

$^1$H-RMN (CDCl$_3$, 300 MHz): δ (ppm)=2.02 (s, 3H, SeCH$_3$); 2.08 (m, 1H); 2.22 (m, 1H); 2.70 (m sym.), 2H); 4.41 (dd, J=8 Hz, J=4 Hz, 1H, α-H).

$^{13}$C-RMN (CDCl$_3$, 75.5 MHz): δ (ppm)=4.1; 20.3; 34.0; 69.9; 178.6.

MS (electrospray): m/z (%)=197 (CH$_3$SeCH$_2$CH$_2$CHOHCO$_2$).

[α]$_D$=18.9±1 (c=1, EtOH).

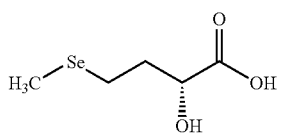

EXAMPLE 5

Preparation of D,L-2-hydroxy-4-methylselenobutyric acid

D,L-2-hydroxy-4-methylselenobutyric acid is obtained using the method described in Example 1, but by adding 0.76 mL (1.0 g, 9.8 mmol) of racemic alpha-hydroxybutyrolactone to the solution of lithiomethylselenolate. Recrystallisation of the raw product in toluene results in D,L-2-hydroxy-4-methylselenobutyric acid with purity >98% (1H-RMN, CDCl$_3$) in the form of a slightly beige powder.

pF (° C.): 49.3-49.9.

$^1$H-RMN (CDCl$_3$, 300 MHz): δ (ppm)=2.02 (s, 3H, SeCH$_3$); 2.08 (m, 1H); 2.22 (m, 1H); 2.70 (m sym.), 2H); 4.41 (dd, J=8 Hz, J=4 Hz, 1H, α-H).

$^{13}$C-RMN (CDCl$_3$, 75.5 MHz): δ (ppm)=4.1; 20.3; 34.0; 69.9; 178.6.

MS (EI, 70 eV): m/z (%)=198 (M$^{+o}$, 80); 123 (40); 103 (60); 103 (60).

R$_f$ (SiO$_2$, cyclohexane/ethyl acetate, 50/50+1% CF$_3$COOH): 0.26.

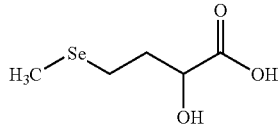

EXAMPLE 6

Synthesis of D,L-2-hydroxy-4-methylselenobutyric acid (10 g-scale)

To a black suspension of selenium (6.45 g, 81.7 mmol) in anhydrous tetrahydrofuran (300 ml), cooled to −6° C. (internal temperature) in an ice-salt bath and under an atmosphere of argon, was added an ethereal solution of methyl lithium (1.6M; 60 ml) dropwise over 40 min, the internal temperature was maintained below 0° C. during the addition. A small amount of white deposit was present on the side of the flask which was washed using additional anhydrous THF (30 ml). After 20 min, 2-hydroxybutyrolactone (7.64 ml, 98.0 mmol) was added, precipitation occurred on addition forming a milky yellow mixture. After a further 10 min the ice bath was removed and the reaction vessel was sealed. After 22 h stirring at room temperature the reaction mixture was heated to 35° C. (internal temperature) and stirred for a further 23 h. The reaction was allowed to cool to room temperature and then further cooled with an ice bath. The mixture was filtered and the solid was washed with TBME (3×100 ml). The yellow solid was dissolved in water (500 ml), the pH of the solution was adjusted to pH=10 using an aqueous solution of sodium hydroxide (2N; ca. 1 ml), the aqueous phase was washed with TBME (200 ml) and then acidified (pH=1) using concentrated hydrochloric acid. The organic material was extracted with TBME (4×200 ml), the organic extracts were combined, dried (Na$_2$SO$_4$), filtered and the solvent removed under reduced pressure to leave D,L-2-hydroxy-4-methylselenobutyric acid (12.14 g, 75%) as a yellow oil, which solidified on cooling to a light yellow solid. The 1H-NMR (CDCl$_3$) is identical to the one obtained in the previous Example 5.

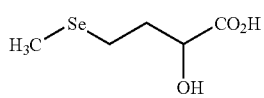

EXAMPLE 7

Synthesis of sodium D,L-2-hydroxy-4-methylseleno-butyrate

To a mixture of sodium hydride (84.6 mg; 60% in mineral oil) and anhydrous THF (2.0 ml), stirred under an atmosphere of argon, was added a solution of the D,L-2-hydroxy-4-methylselenobutyric acid (0.4244 g, 2.15 mmol) in anhydrous THF (2.0 ml) dropwise over 5 min. The solution bubbled vigorously during the addition. A yellow solution together with a small amount of white precipitate was present at the end of the addition. The mixture was cooled in an ice bath and cyclohexane (3 ml) was added this resulted in the formation of a yellow precipitate. The yellow solid was collected, washed with cyclohexane (3 ml) and TBME (3×3 ml) and dried under reduced pressure to leave the sodium salt of the acid (0.3780 g, 1.73 mmol, 82%).

$^1$H-NMR (D$_2$O, 300 MHz): δ(ppm)=1.80-2.07 (m, 5H); 2.45-2.60 (m, 2H); 4.00 (dd, J=4 Hz and 8 Hz, 1H; α-H). Additional signals: 1.12(s); 3.12(s).

$^{13}$C-NMR (D$_2$O, 75.5 MHz): δ(ppm)=3.3; 20.3 (CH$_2$); 34.7 (CH$_2$); 72.0; 180.9 (C=O).

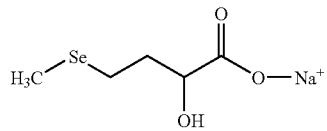

EXAMPLE 8

Synthesis of calcium D,L-2-hydroxy-4-methylseleno-butyrate

To a light yellow solution of the D,L-2-hydroxy-4-methylselenobutyric acid (0.4540 g, 2.30 mmol) in water (0.9 ml) was added calcium hydroxide (81 mg, 1.09 mmol). A large amount of undissolved material was present after the addition. The mixture was diluted with water (1.1 ml), the solid was collected by filtration and washed sequentially with water (3×2 ml) and diethyl ether (3×2 ml). The solid was dried under reduced pressure to leave the desired calcium salt (87.7 mg, 0.20 mmol, 19%) as a white solid.

$^1$H-NMR (D$_2$O, 300 MHz): δ(ppm)=1.88-2.13 (m, 5H); 2.50-2.68 (m, 2H); 4.11 (dd, J=4 Hz and 7 Hz, 1H; α-H). Additional signals: 1.12 (s); 3.12(s).

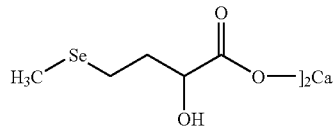

EXAMPLE 9

Synthesis of ethyl-D,L-2-hydroxy-4-methylselenobutyrate

To a colourless solution of the D,L-2-hydroxy-4-methylselenobutyric acid (0.3225 g, 1.64 mmol) in absolute ethanol (6.5 ml), stirred under an atmosphere of argon, was added boric acid (21.1 mg, 0.34 mmol). After 25 h stirring at room temperature, the reaction mixture was heated at reflux and stirred for a further 20 h. TLC indicated that the reaction was not complete, additional boric acid (20.9 mg, 0.34 mmol) was added and the reaction was stirred, at reflux, for a further 4 days. The reaction mixture was allowed to cool to room temperature and the solvent was removed under reduced pressure to leave a light yellow liquid. Saturated aqueous sodium bicarbonate (20 ml) and water (20 ml) were added and the organic material was extracted with diethyl ether (3×40 ml). The extracts were combined, dried (Na$_2$SO$_4$), filtered and the solvent removed under reduced pressure to leave the desired ethyl ester (0.3340 g, 1.48 mmol, 91%) as a light yellow liquid.

$^1$H-NMR (CDCl$_3$, 300 MHz): δ(ppm)=1.30 (t, J=7 Hz, 3H, CH$_2$CH$_3$); overlapping 2.02 (s, 3H, SeCH$_3$) and 1.92-2.08 (m, 1H); 2.08-2.22 (m, 1H); 2.59-2.76 (m, 2H); 2.86 (d, J=5 Hz, 1H, OH); overlapping 4.25 (q, J=7 Hz, 2H, CH$_2$CH$_3$) and 4.22-4.32 (m, 1H, α-H).

$^{13}$C-NMR (CDCl$_3$, 75.5 MHz): δ(ppm)=4.1; 14.2; 20.3; 34.7; 61.9; 69.9; 174.8.

MS (EI, 70 eV): m/z (%)=226 (M$^{+\circ}$, 23); 181 (8); 153 (7); 131 (40); 123 (9); 109 (23); 103 (27); 85 (21); 76(17); 57 (100); 41 (13).

R$_f$(SiO$_2$, ethyl acetate/cyclohexane, 50/50+1% CF$_3$CO$_2$H): 0.61 (stained with phosphomolybdic acid).

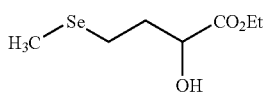

EXAMPLE 10

Synthesis of isopropyl-D,L-2-hydroxy-4-methylselenobutyrate

To a colourless solution of the D,L-2-hydroxy-4-methylselenobutyric acid (0.3284 g, 1.67 mmol) in absolute ethanol (7 ml), stirred under an atmosphere of argon, was added boric acid (42.9 mg, 0.69 mmol). The reaction mixture was heated at reflux and stirred for 3 days. TLC indicated that the reaction was not complete, additional boric acid (23.4 mg, 0.38 mmol) was added and the reaction was stirred at reflux, for a further 16 h. The reaction mixture was allowed to cool to room temperature and the solvent was removed under reduced pressure to leave a light yellow liquid (0.38 g). Saturated aqueous sodium bicarbonate (20 ml) and water (20 ml) were added and the organic material was extracted with diethyl ether (3×30 ml). The extracts were combined, dried (Na$_2$SO$_4$), filtered and the solvent removed under reduced pressure to leave the desired isopropyl ester (0.3384 g, 1.41 mmol, 85%) as a light yellow liquid.

$^1$H-NMR (CDCl$_3$, 300 MHz): δ(ppm)=overlapping 1.28 [d, J=6 Hz, 3H, CH(CH$_3$)$_2$] and 1.28 [d, J=6 Hz, 3H, CH(CH$_3$)$_2$]; overlapping 2.01 (s, 3H, SeCH$_3$) and 1.90-2.07 (m, 1H); 2.07-2.21 (m, 1H); 2.57-2.74 (m, 2H); 2.87 (d, J=5 Hz, 1H, OH); 4.21-4.27 (m, 1H, α-H); 5.10 [septet, J=6 Hz, 1H, CH(CH$_3$)$_2$].

$^{13}$C-NMR (CDCl$_3$, 75.5 MHz): δ(ppm)=4.2; 20.3; 21.7; 21.8; 34.8; 69.8; 70.0; 174.3.

MS (EI, 70 eV): m/z (%)=240 (M$^{+\circ}$, 10); 103 (28); 87 (22); 71(62); 57 (73); 43 (100).

R$_f$ (SiO$_2$, ethyl acetate/cyclohexane, 50/50+1% CF$_3$CO$_2$H): 0.63 (stained with phosphomolybdic acid).

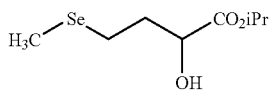

EXAMPLE 11

Synthesis of D,L-2-acetoxy-4-methylselenobutyric acid

To a colourless solution of the D,L-2-hydroxy-4-methylselenobutyric acid (0.3222 g, 1.63 mmol) in anhydrous dichloromethane (27 ml), stirred under an atmosphere of argon, was added acetic anhydride (0.62 ml, 6.57 mmol) followed by addition of a catalytic quantity of DMAP. After 6 h, additional acetic anhydride (0.62 ml, 6.57 mmol) was added and the reaction was stirred overnight. TLC indicated that the reaction was complete, water (10 ml) was added and the dichloromethane was removed under reduced pressure. Saturated aqueous ammonium chloride (40 ml) was added and the organic material was extracted with diethyl ether (3×40 ml). The extracts were combined, dried ($Na_2SO_4$), filtered and the solvent removed under reduced pressure to leave a crude light yellow oil (0.2954 g). The crude oil was purified by column chromatography on silica gel using a mixture of ethyl acetate:cyclohexane (3:7) and 1% TFA as eluent to give the desired acetate (0.1436 g, 0.64 mmol, 40%) as a colourless liquid, and an impure fraction of the acetate [0.1068 g, two spots by TLC: $R_f$(SiO$_2$, ethyl acetate/cyclohexane, 50/50+1% $CF_3CO_2H$): 0.52 and 0.65 and additional peaks in the $^1$H-NMR (CDCl$_3$, 300 MHz): δ(ppm)=2.17 (pseudo d); 5.14-5.22 (m)].

$^1$H-NMR (CDCl$_3$, 300 MHz): δ(ppm)=2.01 (s, 3H); 2.16 (s, 3H); 2.19-2.27 (m, 2H); 2.54-2.69 (m, 2H); 5.16 (t, J=6 Hz, 1H; α-H).

$^{13}$C-NMR (CDCl$_3$, 75.5 MHz): δ(ppm)=4.1; 19.9; 20.5; 31.4; 71.3; 170.4 and 175.1.

MS (EI, 70 eV): m/z (%)=240 (M$^{+o}$, 7); 145 (8); 103 (7); 85 (10); 57 (10); 43 (100).

$R_f$(SiO$_2$, ethyl acetate/cyclohexane, 50/50+1% $CF_3CO_2H$): 0.52 (stained with phosphomolybdic acid).

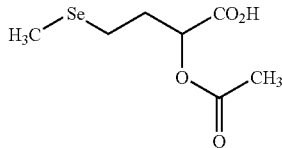

EXAMPLE 12

Synthesis of D,L-2-linoleyloxy-4-methylselenobutyric acid

To a colourless solution of linoleic acid (0.40 ml, 1.28 mmol) in anhydrous DMF (27 ml), stirred under an atmosphere of argon, was added 1-hydroxybenzotriazole (0.1745 g, 1.29 mmol) followed by addition of HCTU (0.5322 g, 1.29 mmol). After 1 h, a solution of the D,L-2-hydroxy-4-methylselenobutyric acid (0.2545 g, 1.29 mmol) in anhydrous DMF (2.4 ml) was added, followed by addition of DIEA (0.44 ml, 2.54 mmol). After 16 h, the reaction was deemed to be complete. The solvent was removed under reduced pressure to leave an orange oil (1.827 g). The crude oil was partitioned between saturated aqueous sodium bicarbonate (25 ml) and diethyl ether (40 ml). The layers were separated and the aqueous phase was washed with further diethyl ether (2×40 ml). The ethereal extracts were combined, dried ($Na_2SO_4$), filtered and the solvent removed under reduced pressure to leave a crude white waxy-solid (0.719 g). The crude material was purified by column chromatography on silica gel using a mixture of ethyl acetate/cyclohexane (3/7) and 0.1% TFA as eluent to give the linoleate (0.0813 g, 0.18 mmol, 14%) as a reddish-orange oil.

$^1$H-NMR (DMSO, 300 MHz): δ(ppm)=0.83 (t, J=7 Hz, 3H); 1.16-1.36 (m, 15H); 1.42-1.59 (m; 2H); overlapping 1.93 (s, 3H, SeCH$_3$) and 1.91-2.10 (m, 6H); 2.28-2.36 (m, 2H); 2.47-2.59 (m, 2H); 2.69-2.78 (m, 2H); 4.91 (dd, J=6 Hz and 7 Hz, 1H, α-H); 5.21-5.39 (m, 4H).

$^{13}$C-NMR (DMSO, 75.5 MHz): δ(ppm)=3.4; 13.9; 19.8; 21.9; 24.3; 25.2; 26.6; 28.3; 28.4; 28.7; 28.9; 30.8; 31.1; 33.2; 71.1; 127.7; 129.7; 170.9; 172.4.

MS (IC, NH$_3$): m/z=478 (M+NH$_4$)$^+$.

$R_f$(SiO$_2$, ethyl acetate/cyclohexane, 30/70+1% $CF_3CO_2H$): 0.53 (stained with KMnO$_4$).

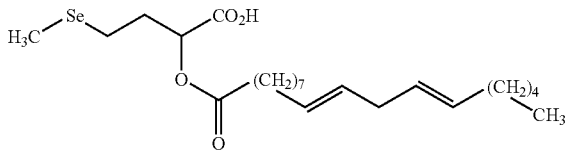

EXAMPLE 13

Synthesis of Di-D,L-2-hydroxy-4-butyric acid diselenide

A dry three-necked round-bottom flask, under an atmosphere of argon, was fitted with a thermometer and a condenser and was charged with selenium (1.3984 g; 17.7 mmol) and sodium borohydride (0.4606 g; 12.2 mmol). The flask was cooled in an ice bath and absolute ethanol (30 ml) was added, on addition an exothermic reaction occurred with vigorous bubbling. After 15 min, the ice bath was removed and the reddish-brown mixture was degassed with argon via a needle. After 20 min, the degassing was stopped and the mixture was heated at reflux. After 2 h at reflux, 2-hydroxybutyrolactone (1.66 ml; 21.3 mmol) was added and the mixture was maintained at reflux for a further 39 h. The orange solution was allowed to cool to room temperature and then cooled in an ice bath, a yellow precipitate formed. Diethyl ether (20 ml) was added resulting in further precipitation. The yellow solid was filtered and washed with diethyl ether (2×50 ml). The solid was dissolved in water (50 ml), the pH of the solution was adjusted to pH=10 using aqueous sodium hydroxide (4N). A small amount of black solid remained undissolved. The mixture was filtered, the aqueous phase was washed with diethyl ether (2×20 ml) and acidified (pH=10) using concentrated hydrochloric acid. The organic material was extracted with diethyl ether (6×30 ml), the fractions combined, dried ($Na_2SO_4$), filtered and the solvent removed under reduced pressure to leave the diselenide [1.40 g, 65%, purity ca. 95%], as a yellow oil.

$^1$H-NMR (D$_2$O, 300 MHz): δ(ppm)=1.98-2.22 (m, 2H); 2.82-2.98 (m, 2H); 4.28 (dd, J=4 Hz and 8 Hz, 1H; α-H).

Additional signals: 1.04 (Et$_2$O); 1.15(t); 3.43 (Et$_2$O); 4.10 (q).

R$_f$(SiO$_2$, ethyl acetate+1% CF$_3$CO$_2$H): 0.57 (stained with phosphomolybdic acid).

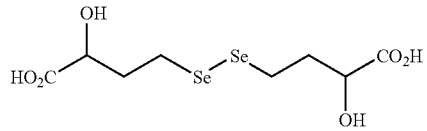

EXAMPLE 14

Preparation of Compositions According to the Invention

Capsules were prepared with the following composition:

| | |
|---|---|
| L-2-hydroxy-4-methylselenobutyric acid | 0.2 mg |
| Excipients* and envelope** | to make a 500 mg capsule |

(*corn starch, lactose, magnesium stearate, sodium lauryl sulphate, **gelatine, titanium dioxide, colouring agents).

Capsules were prepared with the following composition:

| | |
|---|---|
| L-2-hydroxy-4-methylselenobutyric acid | 0.05 mg |
| Excipients* and envelope** | to make a 500 mg capsule |

(*corn starch, lactose, magnesium stearate, sodium lauryl sulphate, **gelatine, titanium dioxide, colouring agents).

Capsules were prepared with the following composition:

| | |
|---|---|
| L-2-hydroxy-4-methylselenobutyric acid | 0.1 mg |
| Excipients* and envelope** | to make a 500 mg capsule |

(*corn starch, lactose, magnesium stearate, flavour, **gelatine, titanium dioxide, colouring agents).

Capsules were prepared with the following composition:

| | |
|---|---|
| Dicyclohexyl ammonium L-2-hydroxy-4-methylselenobutyrate | 0.15 mg |
| Excipients* | to make a 1 g capsule |

(*corn starch,, talc, magnesium stearate).

The invention claimed is:
1. Organoselenium compounds of the general formula (I) comprising:

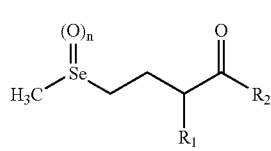

in which
n=0, 1 or 2,
R$_1$=OH, OCOR$_3$, OPO$_3$H$_2$, OPO(OR$_4$)(OR$_5$), or OR$_6$,
R$_2$=OH, R$_3$, or NHR$_7$,
R$_3$=alkoxyl (C$_1$-C$_{26}$), ceramide 1, ceramide 2, ceramide 3, ceramide 4, ceramide 5, ceramide 6a or 6b, S-cysteinyl, or S-glutathionyl, or

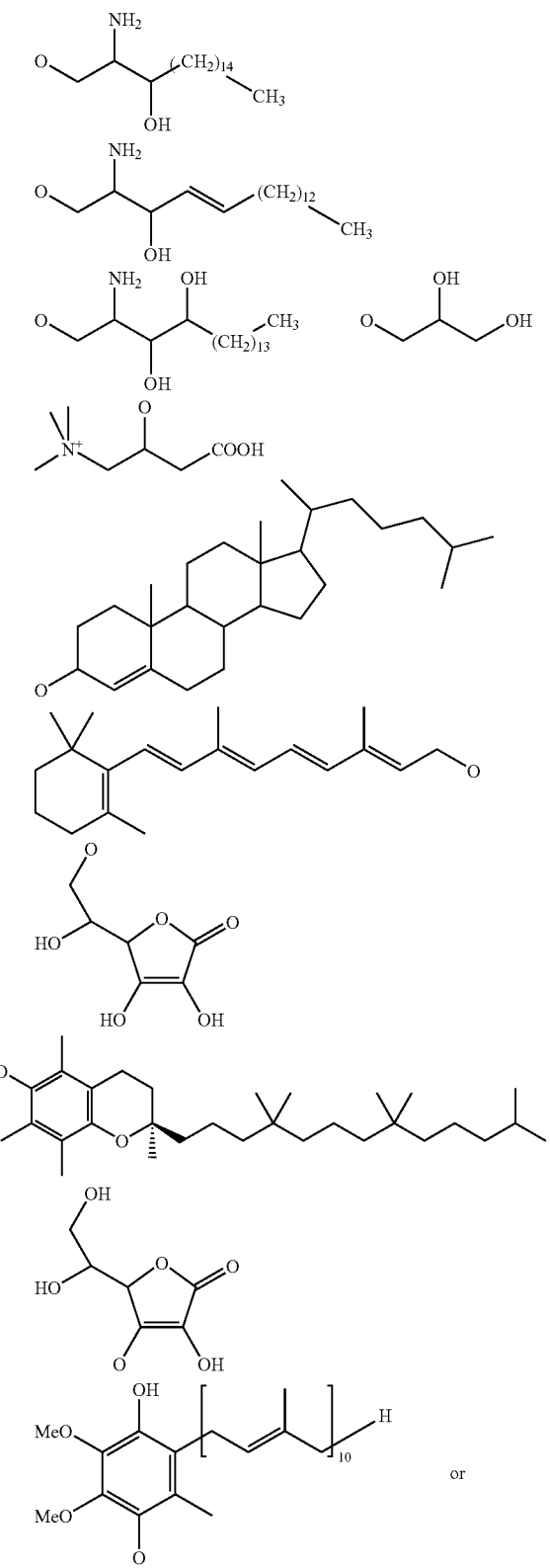

or

OR$_4$=alkoxyl (C$_1$-C$_{26}$), ceramide 1, ceramide 2, ceramide 3, ceramide 4, ceramide 5, ceramide 6a or 6b, OR$_5$=alkoxyl (C$_1$-C$_{26}$), ceramide 1, ceramide 2, ceramide 3, ceramide 4, ceramide 5, ceramide 6a or 6b, $OR_6$=pyruvate, lactate, citrate, fumarate, maleate, myristate, palmitate, stearate, palmitoleate, oleate, linoleate, natural fatty acids, or 13-cis retinoate, $R_7$=H, alkyl ($C_1$-$C_{26}$), natural amino-acids, or natural amines, it being understood that when n=1 and $R_2$=OH, then $R_1$ cannot be OH;

position isomers, geometric isomers, stereo-isomers, diastereoisomers and enantiomers, taken separately or mixed, and all linear or ramified, acyclic or cyclic oligomers and polymers, and their pharmaceutically acceptable acid or base salts.

2. Compounds according to claim 1 wherein n is 0.

3. Compounds according to claim 1 wherein $R_1$ represents OH, $OCOR_3$, or $OR_6$, $R_3$ and $R_6$ being as defined in claim 1.

4. Compounds according to claim 1 wherein $R_1$ is OH.

5. Compounds according to claim 1 wherein $R_2$ is chosen from the group consisting of OH, $NHR_7$, glyceroyl, monoacylglyceroyl, diacylglyceroyl, coenzyme Q, retinoyl, cholesteroyl, alpha-tocopheroyl, carnitinoyl, sphinganine, sphingosine, phyto-sphingosine, ceramide 1, ceramide 2, ceramide 3, ceramide 4, ceramide 5, ceramide 6a or 6b, ascorbate, S-cysteinyl and S-glutathionyl, $R_7$ being as defined in claim 1.

6. Compounds according to claim 1 wherein $R_2$ represents OH.

7. Compounds according to claim 1 of formula (I'), corresponding to the general formula (I) in which
n=0, 1 or 2,
$R_1$=$OCOR_3$, $OPO_3H_2$, $OPO(OR_4)(OR_5)$, or $OR_6$,
$R_2$=$R_3$, or $NHR_7$,
$R_3$=ceramide 1, ceramide 2, ceramide 3, ceramide 4, ceramide 5, ceramide 6a or 6b, S-cysteinyl, or S-glutathionyl, or

31
OR$_4$=alkoxyl (C$_1$-C$_{26}$), ceramide 1, ceramide 2, ceramide 3, ceramide 4, ceramide 5, ceramide 6a or 6b,
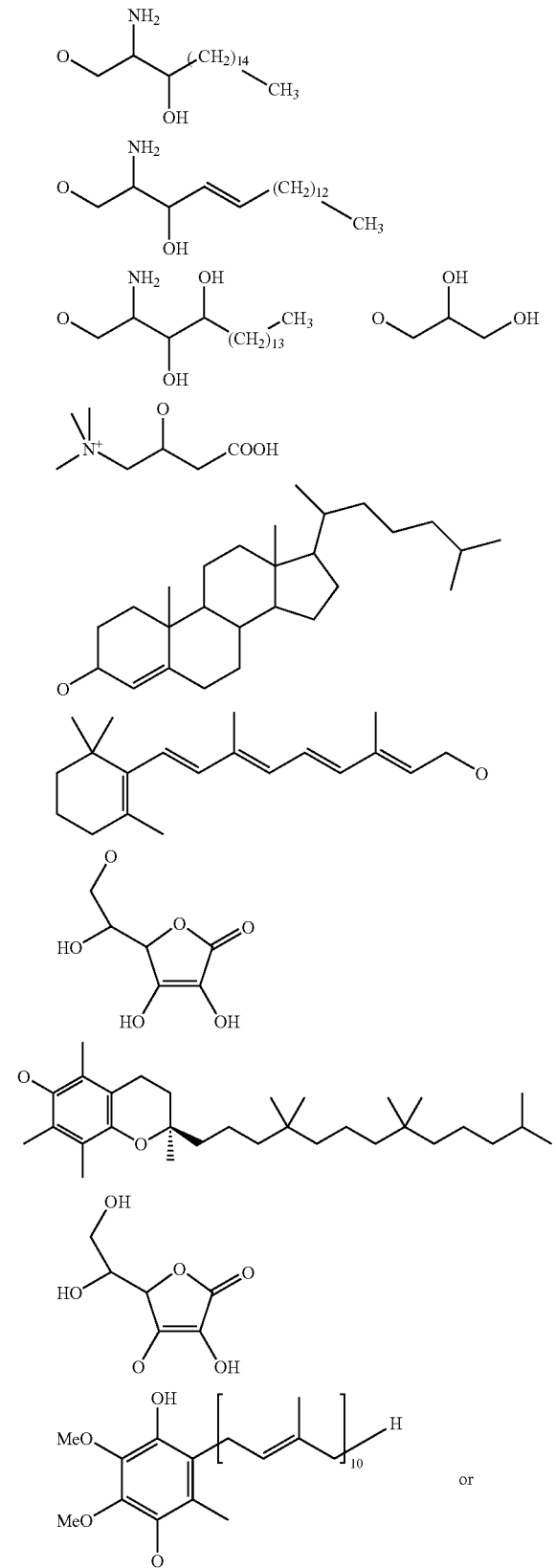
32
-continued
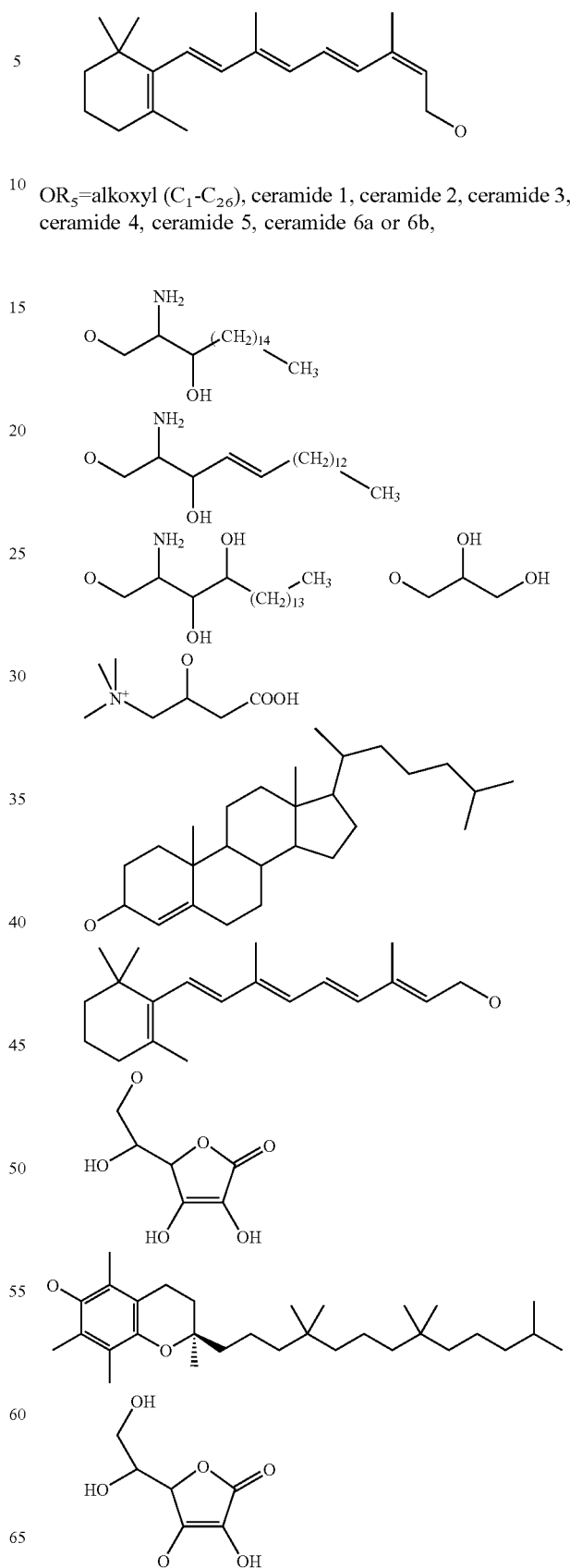
OR$_5$=alkoxyl (C$_1$-C$_{26}$), ceramide 1, ceramide 2, ceramide 3, ceramide 4, ceramide 5, ceramide 6a or 6b, -continued

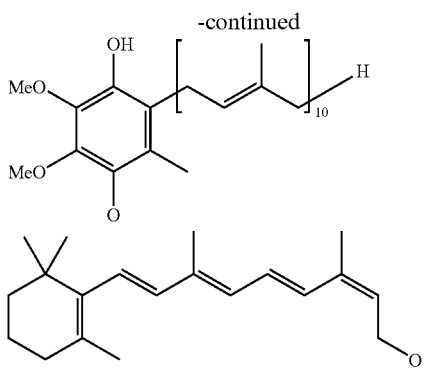
or

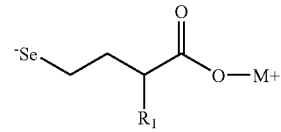

$OR_6$=pyruvate, lactate, citrate, fumarate, maleate, myristate, palmitate, stearate, palmitoleate, oleate, linoleate, natural fatty acids, or 13-cis retinoate, and
$R_7$=H, alkyl ($C_1$-$C_{26}$), natural amino acids, or natural amines.

8. Compounds according to claim 1 of formula (I″), corresponding to the general formula (I) in which
n=0, 1 or 2,
$R_1$=OH,
$R_2$=OH, or $R_3$,
$R_3$=alkoxyl ($C_1$-$C_{26}$),
it being understood that when n=1 and $R_1$=OH, then $R_2$ cannot be OH.

9. Any one of the compounds of general formula I, as defined in claim 1, with the following name:
L-2-hydroxy-4-methylselenobutyric acid,
D-2-hydroxy-4-methylselenobutyric acid,
DL-2-hydroxy-4-methylselenobutyric acid,
dicyclohexylammonium L-2-hydroxy-4-methylselenobutyrate.

10. Compounds according to claim 1 in the form of sodium or calcium or magnesium salts.

11. A process for the preparation of organoselenium compounds of the general formula (I) as defined in claim 1 further comprising at least one of the following steps:

(1) the reaction of (D,L)-2-$R_1$-butyrolactone or one of its enantiomers (D or L), where $R_1$ is as defined in claim 1,
either with an alkaline methylselenolate salt of formula (IIa)

$$CH_3\text{—}Se^-M^+ \quad (IIa)$$

in which M represents an atom of an alkaline metal, to obtain a compound of formula (Ia) in the form of an alkaline salt (Ia)

[structure: $H_3C$—Se—CH$_2$CH$_2$—CH($R_1$)—C(=O)—O$^-$M$^+$]

in which M and $R_1$ are as defined above;
or with an alkaline selenium reagent of formula (IIb)

$$HSe^-M^+ \quad (IIb)$$

in which M represents an atom of an alkaline metal, to obtain a compound of formula (III) in the form of an alkaline salt:

(III)

[structure: $^-$Se—CH$_2$CH$_2$—CH($R_1$)—C(=O)—O$^-$M$^+$]

in which M and $R_1$ are as defined above;
or with an alkaline selenium reagent of formula (IIc)

$$MSeX \quad (IIc)$$

in which M is defined above and X represents a CN radical, or $SO_3M$, or aryl-$SO_2M$, to obtain a compound of formula (IIIa) in the form of an alkaline salt:

(IIIa)

[structure: XSe—CH$_2$CH$_2$—CH($R_1$)—C(=O)—O$^-$M$^+$]

in which M, $R_1$ and X are as defined above;
or with an alkaline selenium reagent of formula (IId)

$$MSeSeM \quad (IId)$$

in which M is as defined above, to obtain a compound of formula (IIIb) in the form of an alkaline salt:

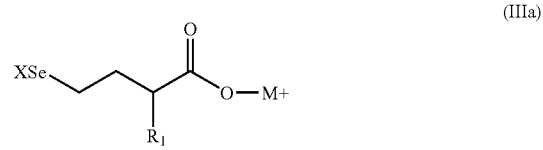

(IIIb)

makes the intermediate compound of formula (IIIa) or (IIIb) react with a reducing agent, to obtain a compound of formula (III)

(III)

[structure: $^-$Se—CH$_2$CH$_2$—CH($R_1$)—C(=O)—O$^-$M$^+$]

and then treats the compound of formula (III) with a methylation agent of formula (IV):

$$CH_3\text{—}Y \quad (IV)$$

in which Y represents a halogen atom, or an $OSO_2CH_3$, $OSO_2$-p-tolyl, or $OCO_2CH_3$ group to obtain the compound of formula (Ia) mentioned above,

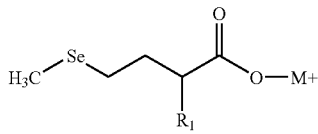

(Ia)

(2) if desired one or even several reactions or series of reactions described below:

acidification of the reaction medium to obtain the acid corresponding to formula (I);

esterification of the acid of formula (I) or its alkaline salt of formula (Ia) with an alcohol or an alkyl halide to obtain the compound of general formula (I) in which $R_2=R_3$ is as defined above;

amidification of the acid of formula (I) or its alkaline salt of formula (Ia) with an appropriate amine of formula $R_7NH_2$, in which $R_7$ is as defined above, to obtain the compound of general formula (I) in which $R_2=NHR_7$ is as defined above;

esterification, when $R_1=OH$, of the hydroxyl function by an appropriate acid to obtain the compound of general formula (I) in which $R_1$ is different from the OH group;

oxidation leading to the selenoxide or selenone derivative to obtain the compound of general formula (I) in which n is equal to 1 or 2;

salification by an acid or a base.

12. A process according to claim 11 wherein the selenium reagent is:

either a methyl selenolate salt which is optionally generated in situ:

or produced from selenium metal Se(0) and an alkyl salt in an aprotic solvent;

or from a dimethyl diselenide $(CH_3Se)_2$ in the presence of a reducing agent;

or a selenocyanate salt which is optionally generated in situ:

or from selenium metal Se(0) and a cyanide salt;

or added to the medium as such, or a selenide or diselenide salt, or a selenosulfate salt.

13. A process according to claim 11 wherein the selenium reagent is lithium methyl selenolate or potassium selenocyanate.

14. As new industrial compounds, (a) compounds of formula

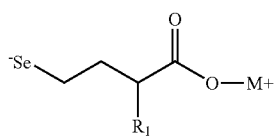

(III)

in which M and $R_1$ are as defined as: (i) $R_1$=OH, $OCOR_3$, $OPO_3H_2$, $OPO(OR_4(OR_5)$, or $OR_6$, wherein $R_3$=alkoxyl $(C_1$-$C_{26})$, ceramide 1, ceramide 2, ceramide 3, ceramide 4, ceramide 5, ceramide 6a or 6b, S-cysteinyl, or S-glutathionyl, or

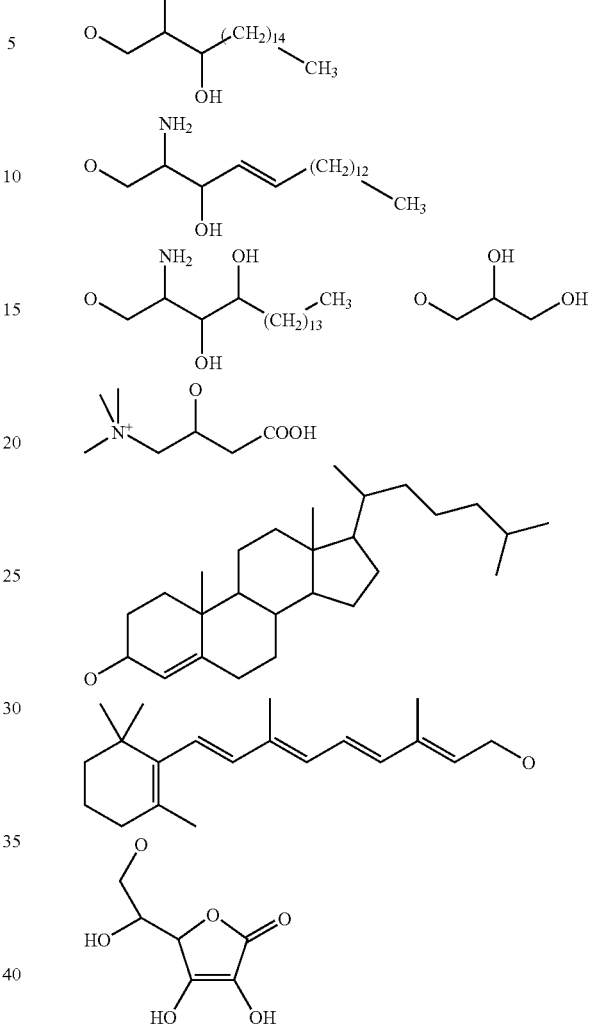

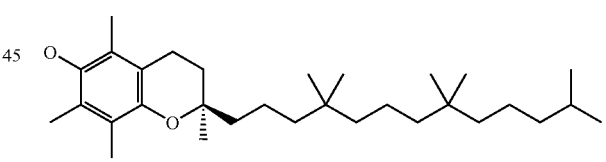

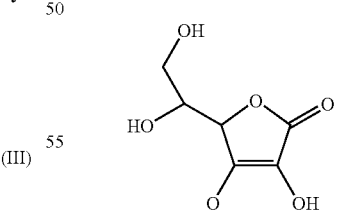

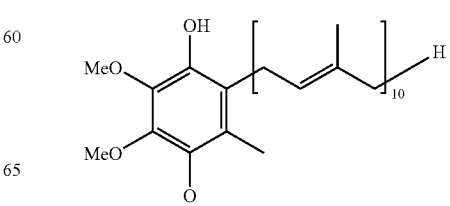

or

-continued
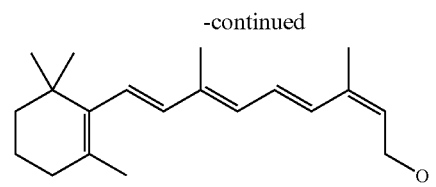
OR₄=alkoxyl ($C_1$-$C_{26}$), ceramide 1, ceramide 2, ceramide 3, ceramide 4, ceramide 5, ceramide 6a or 6b,
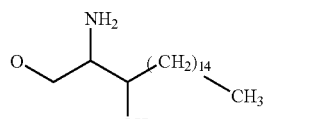
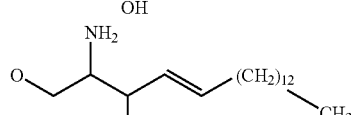
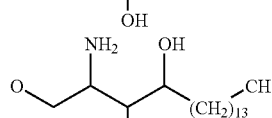
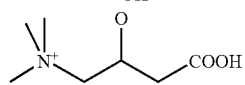
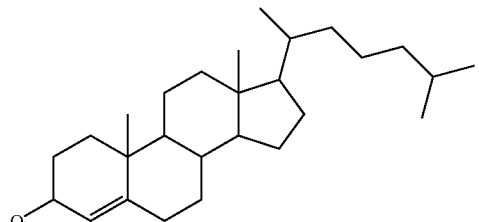
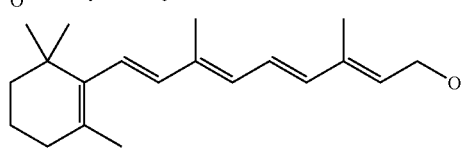
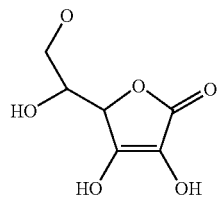
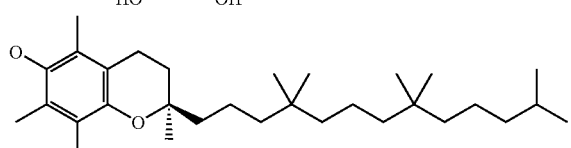
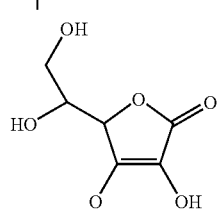
-continued
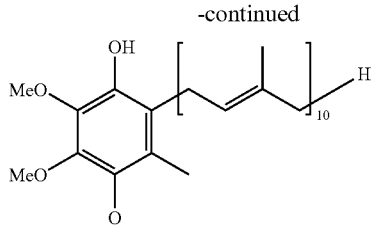
or
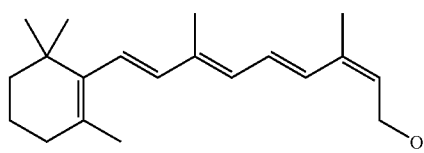
OR₅=alkoxyl ($C_1$-$C_{26}$), ceramide 1, ceramide 2, ceramide 3, ceramide 4, ceramide 5, ceramide 6a or 6b,
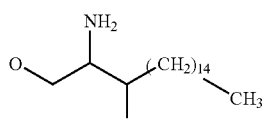
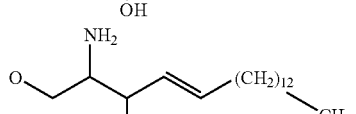
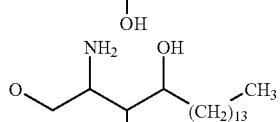
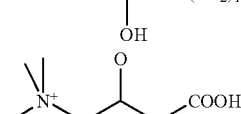
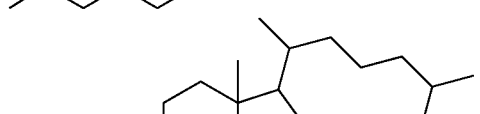
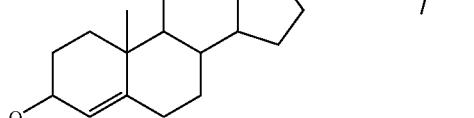
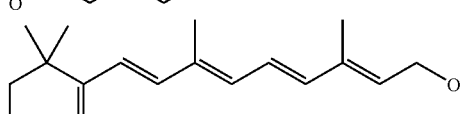
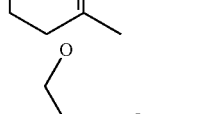
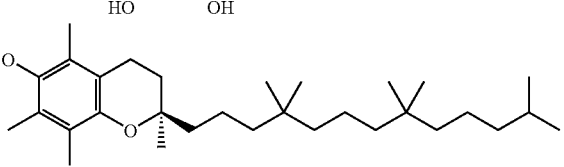

-continued

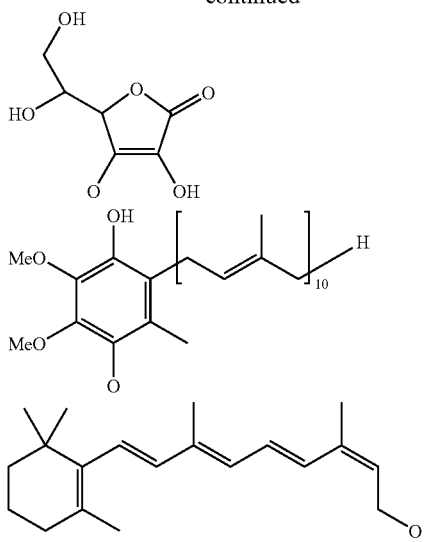

or $OR_6$=pyruvate, lactate, citrate, fumarate, maleate, myristate, palmitate, stearate, palmitoleate, oleate, linoleate, natural fatty acids, or 13-cis retinoate; and (ii) M represents an atom of an alkaline metal (b) compounds of formula:

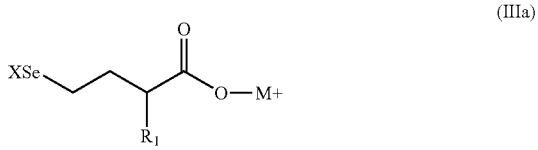

(IIIa)

in which M and $R_1$ are as defined hereinabove and X represents a CN radical, or $SO_3M$, or aryl-$SO_2M$; and (c) compounds of formula:

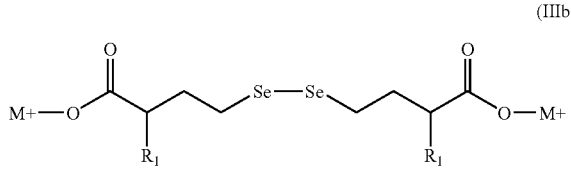

(IIIb)

in which M and $R_1$ are as defined hereinabove.

15. A process for the preparation of L-(+)-selenomethionine starting from 2-hydroxy-4-methylseleno-butyric acid of formula (I) as defined in claim 1, or one of its alkaline salts of formula (Ia),

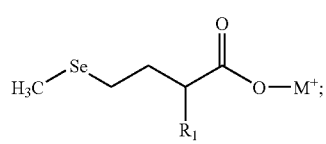

(Ia)

characterized in that it comprises the following steps:
(1) oxidation of 2-hydroxy-4-methylseleno-butyric acid of formula (I) or one of its alkaline salts of formula (Ia), either by an oxido-reductase type enzyme in a buffer with neutral pH, or by a chemical method based on action by an appropriate oxidation reagent to obtain the corresponding ceto-acid of formula (V);

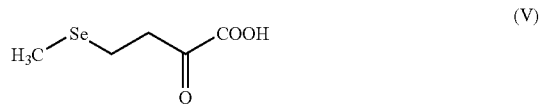

(V)

(2) transamination of the compound of formula (V) either by an enzymatic method using a transaminase, or chemically under reducing amination conditions to obtain L-(+)-selenomethionine.

16. A method for use of compounds of general formula (I) as defined in claim 1, comprising administering to an animal and/or human the compounds of general formula (I), or their salts with pharmaceutically acceptable acids and bases as a source of selenomethionine, L(+) selenomethionine, and/or selenium.

17. A method for use according to claim 16, wherein n is 0 in compounds of general formula (I).

18. A method for use according to claim 16 wherein the compounds of general formula (I) or their salts are administered to the animal and/or human in the form of food complements or additives for human or animal food.

19. A method for use according to claim 16 wherein the compounds of general formula (I) or their salts are administered to the animal and/or human in the form of complements or additives for cosmetic products.

20. A method for use of the compounds according to claim 7, wherein the method comprises administering to an animal and/or human cosmetic products comprising compounds corresponding to the general formula (I').

21. A method for use according to claim 16 wherein the compounds of general formula (I) or their salts are administered as drugs.

22. A method for use of the compounds according to claim 7, the method comprising administering to an animal and/or human drugs comprising the compounds corresponding to the general formula (I').

23. A method for use of the compounds according to claim 8, the method comprising administering to an animal and/or human food complements or additives for human or animal food comprising compounds of the general formula (I'').

24. Nutritional compositions containing at least one of the compounds of formula (I) as defined claim 1 as an active constituent or additive.

25. Nutritional compositions containing at least one of the compounds of formula (I'') as defined in claim 8 or at least one of their sodium or calcium or magnesium salts, as an active constituent or additive.

26. Cosmetic compositions containing at least one of the compounds of formula (I) as defined in claim 1, as an active constituent or additive.

27. Cosmetic compositions containing at least one of the compounds of formula (I') as defined in claim 7, as an active constituent or additive.

28. Pharmaceutical compositions containing at least one of the compounds of formula (I) as defined in claim 1, as an active constituent or additive.

29. Pharmaceutical compositions containing at least one of the compounds of formula (I') as defined in claim 7, as an active constituent or additive.

30. An organoselenium compound having general formula (I) comprising:

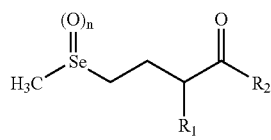

where
n=0;
$R_1$=OH; and $R_2$=OH; a position isomer, a geometric isomer, a stereoisomer, a diastereoisomer, an enantiomer, a linear polymer or oligomer, a ramified polymer or oligomer, an acyclic polymer or oligomer, a cyclic polymer or oligomer, a pharmaceutically acceptable acid or base, or salt thereof.

31. A process according to claim 11, wherein the selenium reagent is:

either a methyl selenolate salt which is optionally generated in situ:
or produced from selenium metal Se(0) and an alkyl salt in an aprotic solvent comprising tetrahydrofurane (THF);
or from a dimethyl diselenide $(CH_3Se)_2$ in the presence of a reducing agent comprising sodium borohydride in an aprotic solvent comprising THF;
or a selenocyanate salt comprising potassium selenocyanate which is optionally generated in situ:
or from selenium metal Se(0) and a cyanide salt comprising potassium cyanide,
or added to the medium as such,
or a selenide or diselenide salt comprising sodium or lithium selenide or diselenide,
or a selenosulfate salt comprising sodium selenosulfate.

32. A method for use according to claim 16 comprising administering to an animal and/or human the compounds of general formula (I), or their salts with pharmaceutically acceptable acids and bases as a source of L(+) selenomethionine.

* * * * *